Figure 1:
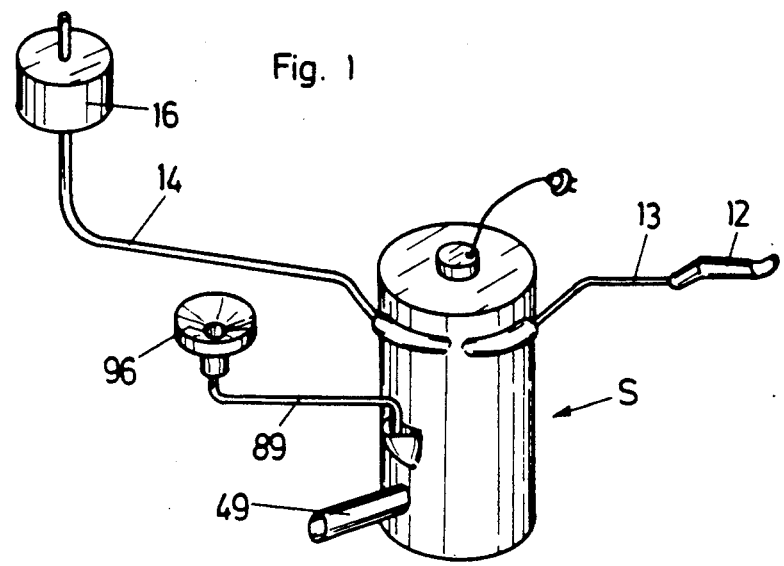

United States Patent [19]

Trawöger et al.

[11] Patent Number: 5,018,971
[45] Date of Patent: May 28, 1991

[54] SEPARATOR

[76] Inventors: Werner Trawöger, Höttinger Au 60, A-6020 Innsbruck; Bruno Pregenzer, Huebe 30, A-6173 Oberperfurss, both of Austria

[21] Appl. No.: 370,152

[22] Filed: Jun. 22, 1989

Related U.S. Application Data

[63] Continuation of Ser. No. 170,443, Mar. 18, 1988, abandoned, which is a continuation-in-part of Ser. No. 905,564, Aug. 11, 1986, abandoned.

[30] Foreign Application Priority Data

Dec. 17, 1984 [AT] Austria .................. 3986/84
Dec. 17, 1984 [AT] Austria ............ PCT/AT85/00057

[51] Int. Cl.⁵ .............................................. A61C 17/06
[52] U.S. Cl. .................................................... 433/92
[58] Field of Search ................. 433/92; 55/192, 421, 55/492

[56] References Cited

U.S. PATENT DOCUMENTS

| | | | |
|---|---|---|---|
| 2,759,476 | 12/1954 | Henderson | 128/278 |
| 3,051,175 | 8/1962 | Nugent | 128/276 |
| 3,078,579 | 2/1963 | Jones et al. | 32/33 |
| 3,138,873 | 6/1964 | Bishop | 32/33 |
| 3,777,403 | 12/1973 | Ritchie | 32/33 |
| 3,847,573 | 11/1974 | Gandrud | 433/92 |
| 3,861,584 | 1/1975 | Dudrey | 233/7 |
| 3,870,483 | 3/1975 | Ritzler | 433/92 |
| 4,234,325 | 11/1980 | Rea | 55/185 |
| 4,332,560 | 6/1982 | Rait | 433/92 |
| 4,385,891 | 5/1983 | Ligotti | 433/92 |
| 4,684,345 | 8/1987 | Cattani | 55/421 |

FOREIGN PATENT DOCUMENTS

| | | |
|---|---|---|
| 0013667 | 1/1980 | European Pat. Off. |
| 0023036 | 10/1983 | European Pat. Off. |
| 0082247 | 7/1985 | European Pat. Off. |
| 0100327 | 8/1985 | European Pat. Off. |
| 0108983 | 2/1986 | European Pat. Off. |
| 0224232 | 6/1987 | European Pat. Off. |
| 0224233 | 6/1987 | European Pat. Off. |
| 0237708 | 9/1987 | European Pat. Off. |
| 2342543 | 10/1975 | Fed. Rep. of Germany |
| 2459881 | 4/1979 | Fed. Rep. of Germany |
| 3030614 | 3/1981 | Fed. Rep. of Germany |
| 8314829 | 10/1983 | Fed. Rep. of Germany |
| 3231272 | 2/1984 | Fed. Rep. of Germany |
| 3521929 | 1/1986 | Fed. Rep. of Germany |
| 2713321 | 2/1987 | Fed. Rep. of Germany |
| 8702001 | 5/1987 | Fed. Rep. of Germany |
| 3542114 | 6/1987 | Fed. Rep. of Germany |
| 3542134 | 6/1987 | Fed. Rep. of Germany |
| 835068 | 12/1938 | France |
| 427988 | 3/1983 | Sweden |
| 1106858 | 3/1968 | United Kingdom |
| 1220255 | 1/1971 | United Kingdom |
| 2045640 | 3/1980 | United Kingdom |

Primary Examiner—Cary E. Stone
Attorney, Agent, or Firm—Lorusso & Loud

[57] ABSTRACT

For the separation of a mixture of solids and liquids, which is produced in dental suction units, a separator is used which comprises a housing in which a mixture inlet, a liquid collecting chamber and a lower sedimentation chamber are provided. A drain opening for clarified liquid is associated with the liquid collecting chamber. The drain opening is arranged above a maximum settling level of the solids, and a first section of a drain line extends vertically upwards from the drain opening. To eliminate disturbance of the settling of solids in the sedimentation chamber to the greatest possible extent, the collected clarified liquid is discharged in each case, when a predetermined flood level of the first section of the drain line is reached. The sedimentation chamber is formed in a removable collector bowl so that the collected solids can be discharged. The separator housing may further be provided with an air separator chamber for separating the suction air from the dental mixture, and a solid bowl centrifuge is preferably provided which separates solid residues from the clarified liquid which are transferred into the collector bowl.

124 Claims, 17 Drawing Sheets

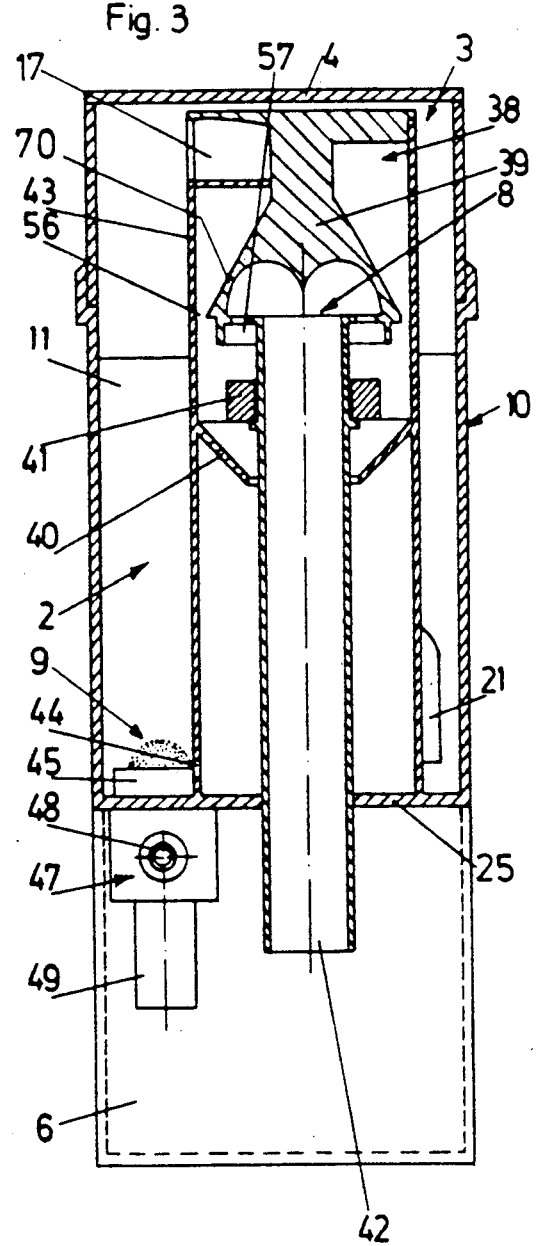

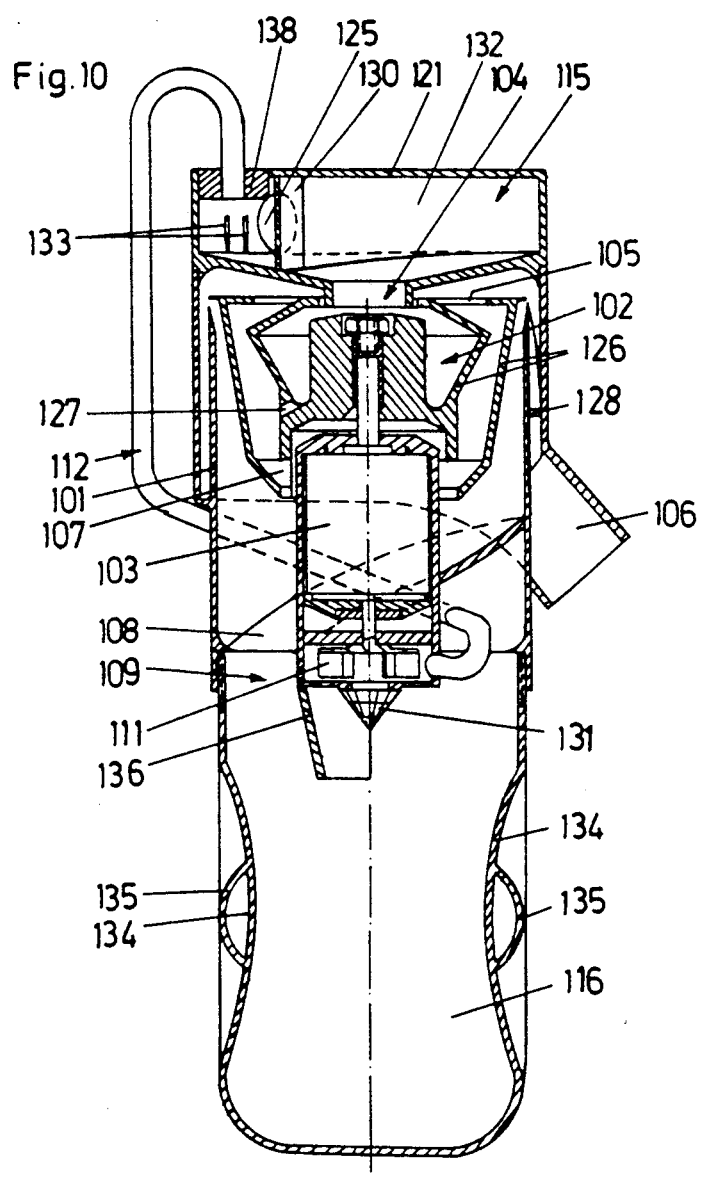

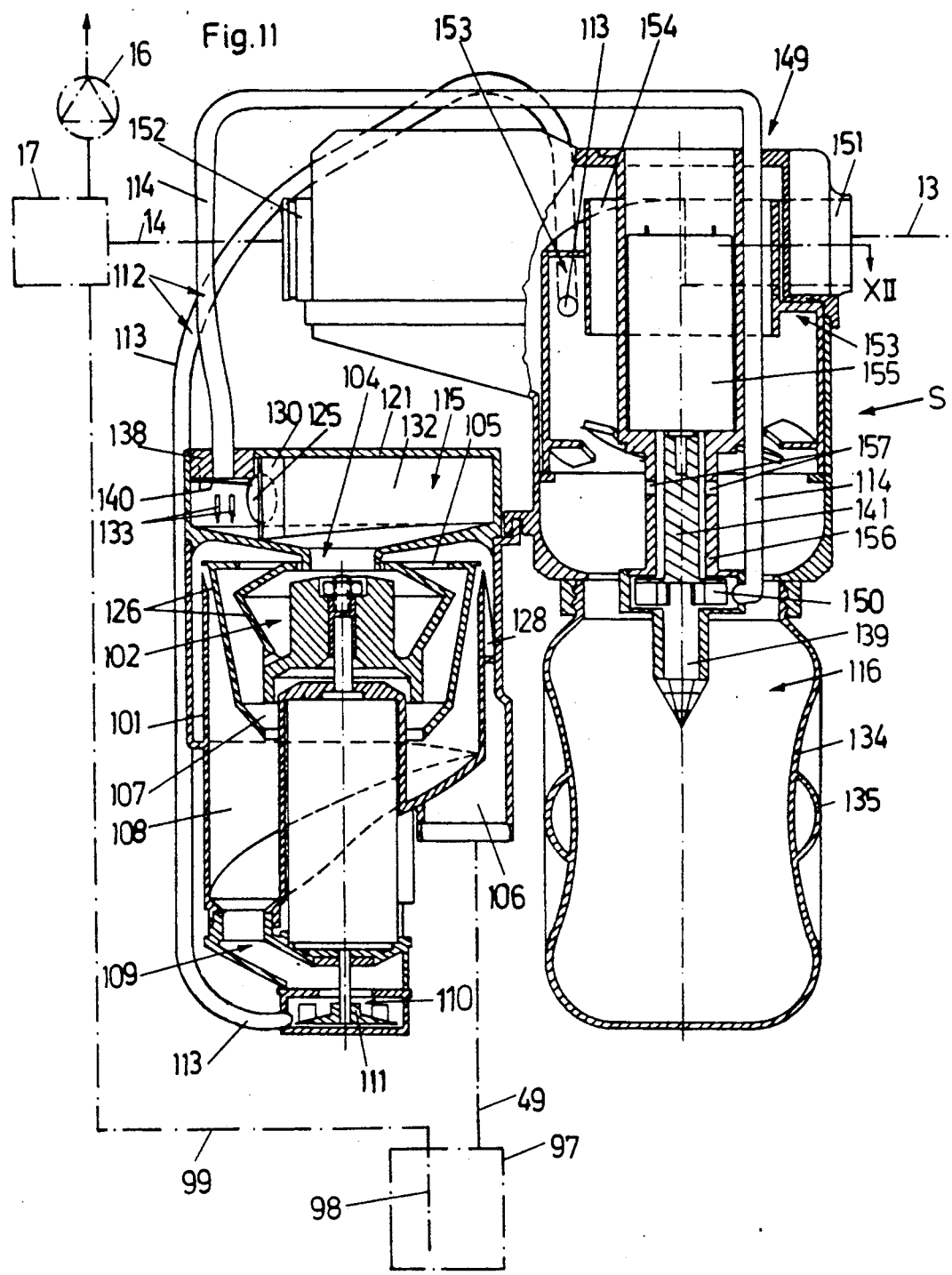

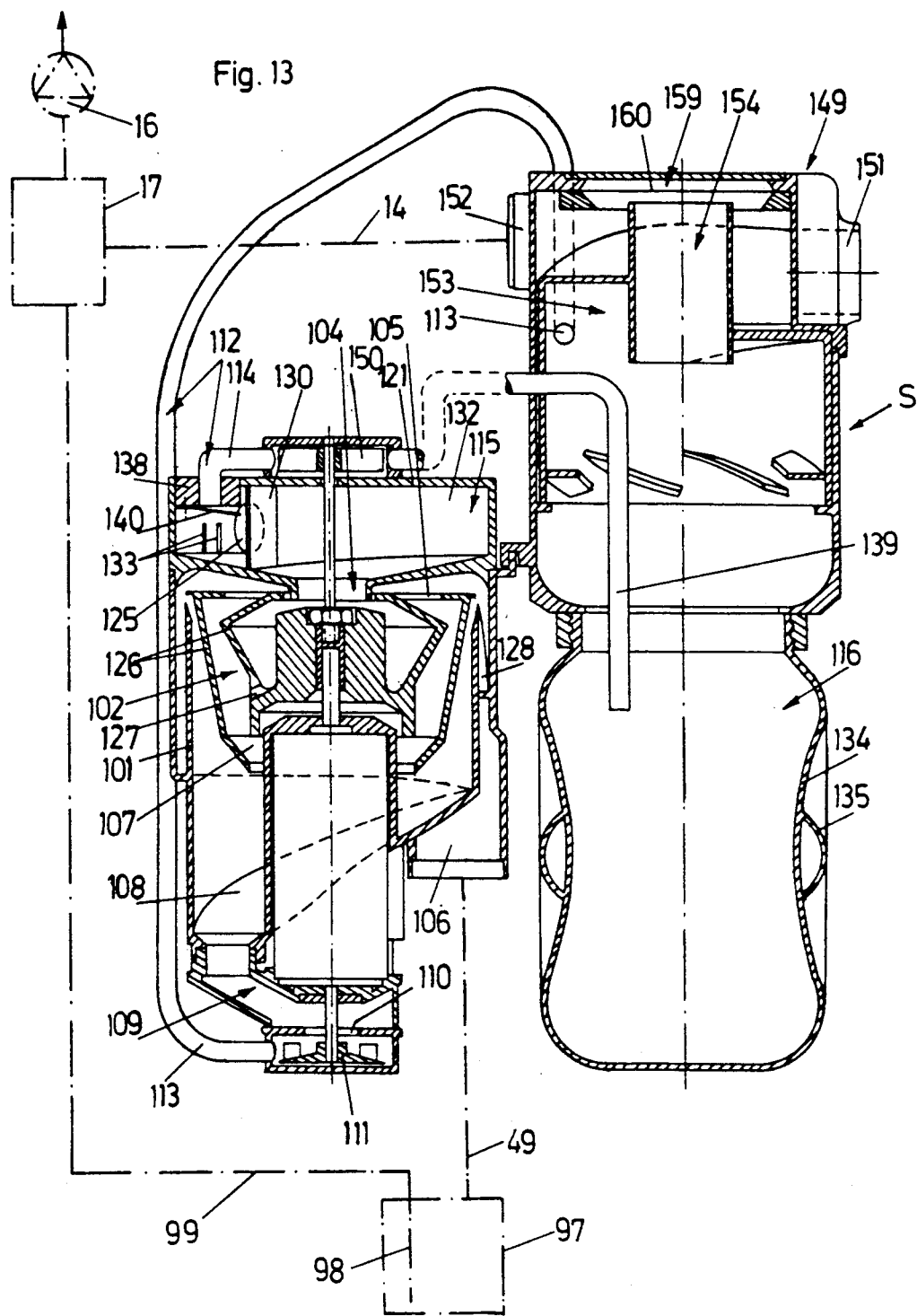

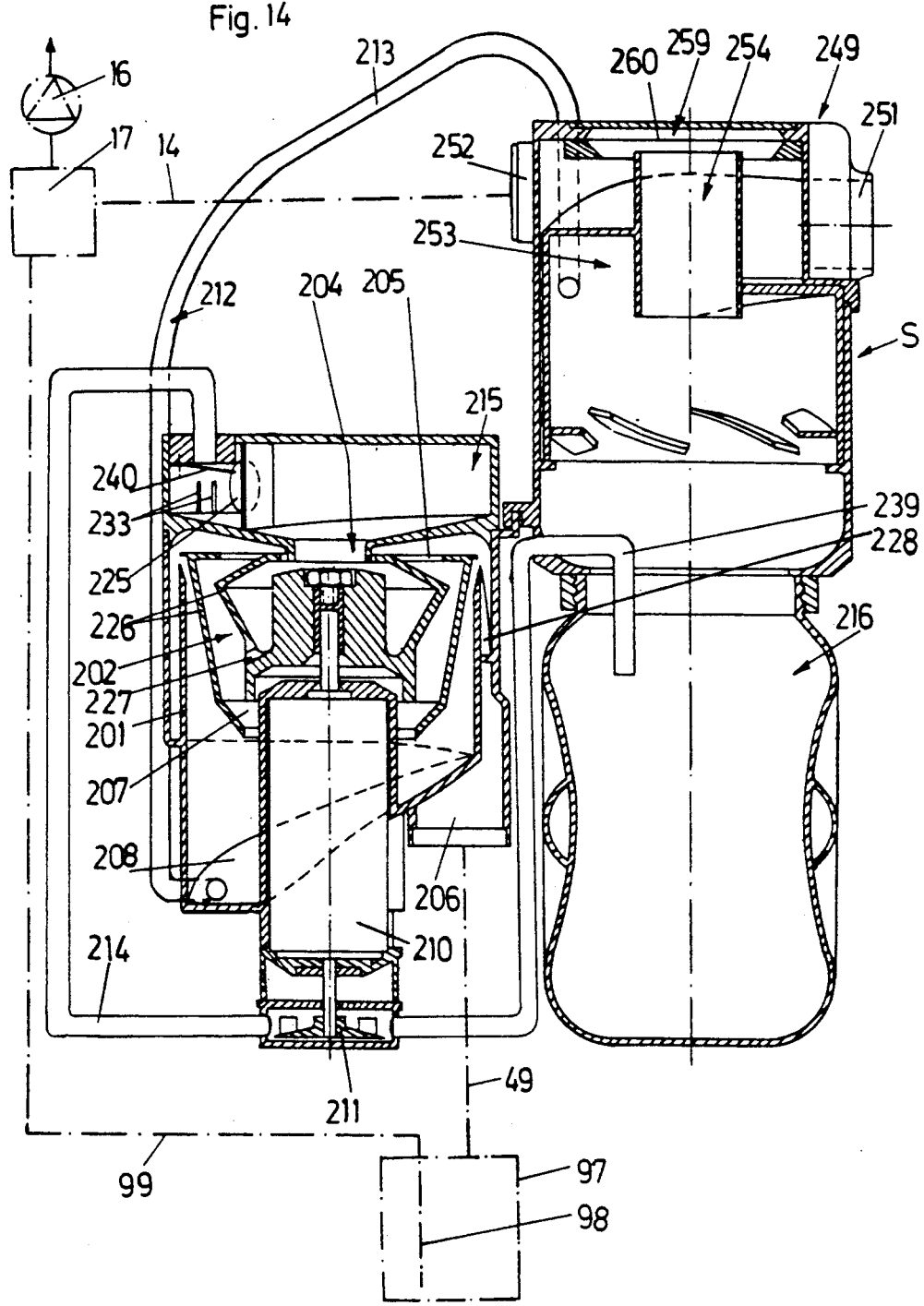

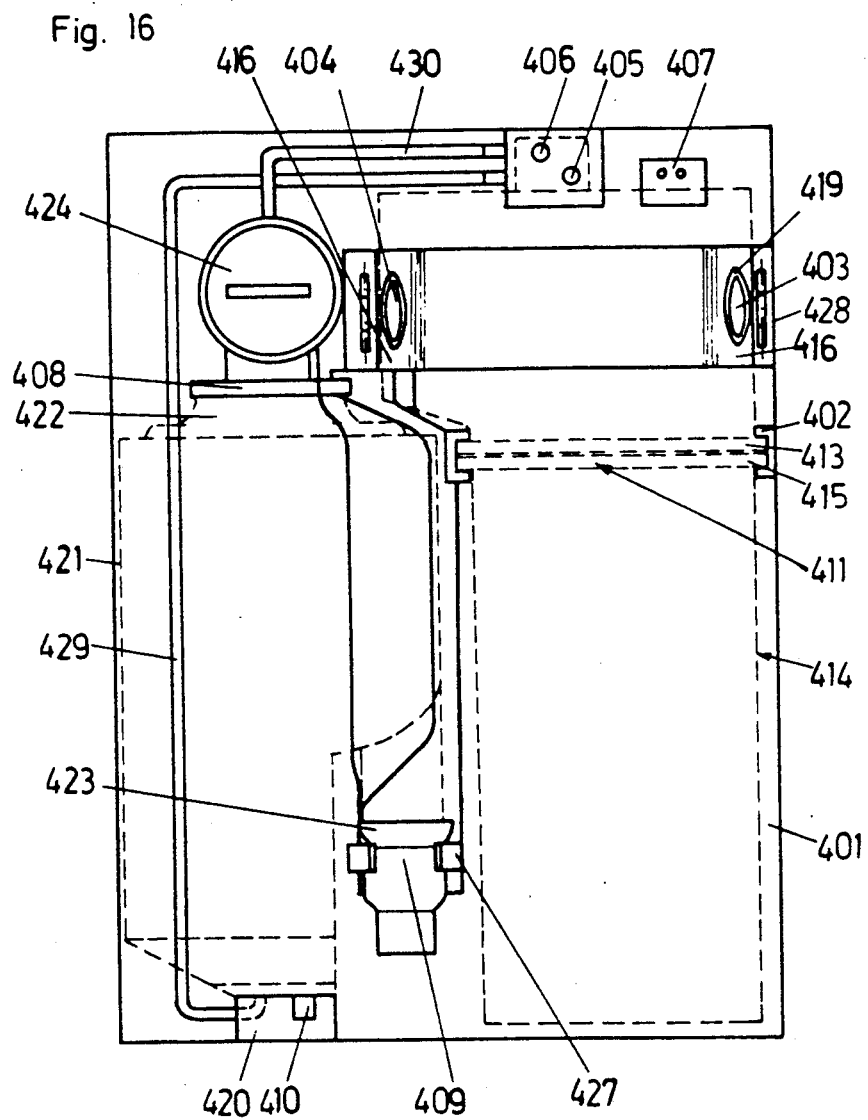

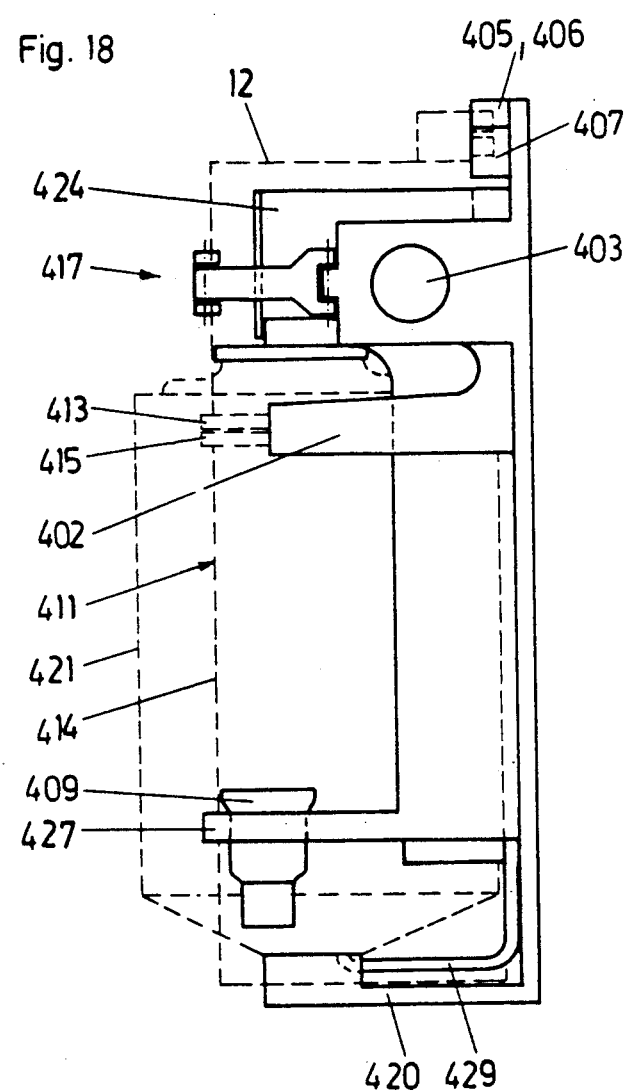

SEPARATOR

This is a continuation of co-pending application Ser. No. 07/170,443, filed on Mar. 18, 1988, now abandoned, which is a continuation-in-part of U.S. Ser. No. 905,564, filed Aug. 11, 1986, now abandoned.

The invention relates to a separator for separating a mixture of solids and liquids being produced in dental suction systems having a suction pump and a suction nozzle discharging said mixture out of a patient's mouth by means of suction air.

A separator of this kind is described, for example, in U.S. Pat. No. 3,847,573. This has a cylindrical housing, through the cover of which, at the centre, discharge one or a plurality of suction lines from suction handpieces such as saliva suctions, into a section of pipe that is open at the bottom. The suction air passes around the lower end of the pipe section and then upwards, so that clean air leaves the separator and any solids and liquids carried along in the suction flow collect at the base of the housing. A liquid outlet is provided in the walls of the housing, at a distance from its base, and this outlet incorporates a oneway valve. Liquid can be drained off from the separator through this valve at intervals. The lower part of the housing can be removed so that the solids can be discharged. It has been shown that the liquid that is to be drained off through the liquid outlet cannot be kept free of solids since, on the one hand, the suction air that has to be vortexed above the level of the liquid so as to be cleaned, and on the other the suction that is generated when the liquid is drained off prevents the complete sedimentation of fine particles. Because of the unusual composition of the liquid (blood, water, saliva) it is impossible to keep the one-way valve in a serviceable state unless it is thoroughly cleaned after each occasion when liquid is drained off. In order to keep the interval between cleanings as long as possible, the separator is in the form of a large vessel, and this has to be accommodated in the treatment room. Furthermore, when dimensions as large as this are involved, it becomes difficult to sterilize the separator properly.

For this reason, there have been numerous proposals to configure the separator as a part of the treatment apparatus. DE-OS 27 13 321 describes a separator that can be incorporated in a treatment unit; this separator is used for separating off clean air, and swirls the suction mixture by means of a cyclone arrangement and collects the solid and the liquid components in a collector. When a predetermined level is reached, a float that is arranged in this system acts through a complex valve mechanism to open a transfer chamber that is located underneath, the outlet of which is closed, in order to prevent the induction of ambient air. Thus, the mixture of solids and liquids can flow into the transfer chamber. The float thus falls and initiates closing of the collector and the opening of the transfer chamber, so that the solid-liquid mixture can run off to the drain, while more liquid collects in the collector. Of course, there is an everpresent danger that the two valves through which the solid-liquid mixture must pass will become unserviceable, and there is also an important disadvantage in the complicated construction of the separator and the considerable number of components.

A similar separator is described in EP-PS 23036 in which a cyclone arrangement is also used to separate a mixture into clean air and solids-liquids mixture. At the outlet for the mixture of solids and liquids there is a pump which, despite the maintenance of the suction flow through the clean air evacuation pump, continuously draws off the solid-liquid mixture. A water jet pump or a centrifugal pump is used for this pump. Since neither type is capable of delivering mixtures containing larger particles of solids, it is essential to incorporate a coarse filter or sieve in the suction mixture channel.

In this version, too, there is the problem of solids passing through the pump.

Removable collectors that are connected to a handpiece are known (U.S. Pat. Nos. 3,777,403, 3,432,560, 4,385,891) and are used in order to extract the metals such as gold, silver and mercury that are present among the solids. The air-liquids mixture is drawn off from this collector, which of necessity contains light particles of solids, since the liquid cannot settle down in the collector.

As described in DE-A- 32 31 272 and 32 42 212, attempts have been made to separate the metals from the solids-liquids mixture after it has passed through the pump that empties the trap, to which end a siphon-type collector is used in conjunction with the trap, that can also have filter inserts. Without filter inserts only medium particles will settle, since large particles cannot pass through the pump and small particles cannot settle because of the flow; the foregoing means that the yield will be small. However, it is now the object of the invention to develop a separator of the above-mentioned kind with the simplest possible design and permitting optimal separation at the same time so that all solids can settle in a collector bowl of the separator without pre- and post-filters. Thus particularly high operational reliability is imparted to the liquid outlet, which is secured against the ingress of unwanted air. Clean, which means solid-free liquid which can readily be discharged into the drain pipe or be admixed again to the clean air shall also be recovered from the solid-liquid mixture separated from the clean air. A further object is to embody the separator in such a manner that removal and exchange of the full collector bowl can be carried out in a simple way, and that service operations at the separator are possible without substantial standstill periods and without essential disturbance of the dentist's work.

According to the invention this is achieved by means of several embodiments:

A first embodiment of a separator to be inserted into the suction line is provided with:
i) a separator housing comprising
   an upper air separating chamber having deflectors,
   an inlet for the mixture to be connected to the first section of the suction line, and an outlet for the separated clean air to be connected to the second section of the suction line,
   an intermediate liquid collecting chamber having a drain opening,
   a lower sedimentation chamber for settling the solids up to a predetermined maximum settling level, and
   a detachable collector bowl embodying the sedimentation chamber, the upper edge of the collector bowl being above the drain opening;
ii) a drain line between the liquid collecting chamber and a liquid outlet at the end of the drain line, said drain line comprising
   several sections, a first section extending upwardly in the liquid collecting chamber, being provided with the drain opening above the predetermined settling level of the solids, and being submersible by accumulated liquid up to a predetermined maximum flood level, and a non-return valve mean$ being arranged in a further section of the drain line and securing against an ingress of unwanted air into the separator housing; and iii) a drain system integrated within the drain line, said system discharging liquid that is accumulated up to the predetermined flood level out of the liquid collecting chamber and transferring said liquid to the liquid outlet.

A further embodiment of a separator to be inserted into the suction line is provided with:

i) a separator housing comprising an upper air separating chamber having deflectors, an inlet for the mixture to be connected to the first section of the suction line, and an outlet for the separated clean air to be connected to the second section of the suction line, an intermediate liquid collecting chamber having a drain opening, a lower sedimentation chamber for settling the solids up to a predetermined maximum settling level, and a detachable collector bowl embodying the sedimentation chamber, the upper edge of the collector bowl being above the drain opening;

ii) a drain line between the liquid collecting chamber and a liquid outlet at the end of the drain line, said drain line comprising several sections, a first section being arranged in the liquid collecting chamber and provided with the drain opening above the predetermined settling level of the solids, said drain opening being submersible by accumulated liquid up to a predetermined maximum flood level, a non-return valve means being arranged in a further section of the drain line and securing against an ingress of unwanted air into the separator housing, and a last section, a centrifuge housing being inserted into the last section of the drain line and having an inlet chamber and a discharge channel terminating at the liquid outlet, the non-return valve means being arranged between the first and the last section of the drain line;

iii) a pump means arranged in the drain line, said pump means discharging liquid that is accumulated up to the predetermined flood level out of the liquid collecting chamber and transferring said liquid to the inlet chamber of the centrifuge housing; and iv) a solid bowl centrifuge arranged in the centrifuge housing, said solid bowl centrifuge being provided with a bottom outlet vertically discharging by gravity solids and liquid residues after each working phase of the centrifuge, and with a top liquid outlet passing cleaned liquid into the discharge channel.

In all embodiments the drain opening for the liquid is arranged at the highest possible position in the separator housing so that the collector bowl thereof thus becomes an effective stabilizing tank. Thus the liquid can be removed from a clarified zone.

A first line section of the device for discharging the clarified liquid may, for example, be formed by a siphon which facilitates the complete sedimentation of the solid particles in the collector bowl since the overflow of liquid takes place at intervals, and the inlet side of the siphon is located below the level of the water when the overflow of liquid starts.

In a further possibility a pump is associated with the drain line and sucks off the clarified liquid. In this arrangement the first line section is an upwardly extending suction tube. The non-return valve is advantageously arranged at the pressure side of the pump so that substantially solid-free liquid flows therethrough. Means measuring the conductance of the liquid may be provided to control the pump.

A water jet pump may for example be used as the pump. Since a pump of this kind requires a relatively great amount of water, an especially favourable configuration of the separator results if an electric vane-type impeller pump is provided as the pump and the non-return valve is associated with the pressure side thereof. Hence, the solid bowl centrifuge can be inserted into the drain line after the pump, and the drain line of the spittoon can run into the centrifuge inlet chamber because the vacuum system in the separator housing is secured against the ingress of air by means of the non-return valve.

The centrifuge also permits the recovery of extremely fine solid particles even at an extremely high flow rate through the sedimentation chamber, which disrupts the complete separation of the solid particles, and additionally those solid portions are recovered, too, which flow off through the spittoon.

A third embodiment of a separator to be inserted into the suction line is provided with:

i) a support having a first line connector to be coupled to the first section of the suction line and a second line connector to be coupled to the second section of the suction line;

ii) a separator housing detachably arranged on the support and comprising an air separating chamber designed as an upper part of the separator housing, the upper part having deflectors, an inlet for the mixture, and an outlet for the separated clean air, said inlet and said outlet tightening to said first and second line connectors, when the separator housing is attached to the support, a liquid collecting chamber being arranged beneath the air separating chamber and having a drain opening, and a sedimentation chamber for settling the solids up to a predetermined maximum settling level, the sedimentation chamber being provided in a collector bowl detachably mounted on the upper part of the separator housing, the upper edge of the collector bowl being above the drain opening;

iii) a drain line between the liquid collecting chamber and a liquid outlet at the end of the drain line, said drain line comprising several sections, a first section extending upwardly in the liquid collecting chamber, being provided with the drain opening above the predetermined settling level of the solids, and being submersible by accumulated liquid up to a predetermined maximum flood level, and a non-return valve means being arranged in a further section of the drain line and securing against an ingress of unwanted air into the separator housing; and iv) a drain system integrated within the drain line, said system discharging liquid that is accumulated up to the predetermined flood level out of the liquid collecting chamber and transferring said liquid to the liquid outlet.

A fourth embodiment of a separator to be inserted into the suction line is provided with:

i) a support having a first line connector to be coupled to the first section of the suction line and a second line connector to be coupled to the second section of the suction line;

ii) a separator housing detachably arranged on the support and comprising
an air separating chamber designed as an upper part of the separator housing, the upper part having deflectors, an inlet for the mixture, and an outlet for the separated clean air, said inlet and said outlet tightening to said first and second line connectors, when the separator housing is attached to the support,
a liquid collecting chamber being arranged beneath the air separating chamber and having a drain opening, and
a sedimentation chamber for settling the solids up to a predetermined maximum settling level, the sedimentation chamber being provided in a collector bowl detachably mounted on the upper part of the separator housing the upper edge of the collector bowl being above the drain opening;

iii) a drain line between the liquid collecting chamber and a liquid outlet at the end of the drain line, said drain line comprising
several sections, a first section extending upwardly in the liquid collecting chamber, being provided with the drain opening above the predetermined settling level of the solids, and being submersible by accumulated liquid up to a predetermined maximum flood level,
a non-return valve means being arranged in a further section of the drain line and securing against an ingress of unwanted air into the separator housing, and
a last section terminating at the liquid outlet, a centrifuge housing, that has an inlet chamber and a discharge channel, being detachably inserted into the last section of the drain line and carried by a support plate of the support, the non-return valve means being arranged between the first and the last section of the drain line;

iv) a pump means arranged in the drain line, said pump means discharging liquid that is accumulated up to the predetermined flood level out of the liquid collecting chamber and transferring said liquid to the inlet chamber of the centrifuge housing; and v) a solid bowl centrifuge arranged in the centrifuge housing, said solid bowl centrifuge being provided with a bottom outlet vertically discharging by gravity solids and liquid residues after each working phase of the centrifuge, and with a top liquid outlet passing cleaned liquid into the discharge channel.

In these arrangements the collector bowl or the complete separator can be removed or exchanged without difficulty because each inlet and outlet of the housing which is fitted into the support is connected with a line connector of the support. When the collector bowl or the separator are removed, only the individual inlet and outlet openings for the flowing media are unclosed. No parts project into the open space so that a contamination of the surrounding areas is almost excluded. When the collector bowl or the separator is mounted, all inlet and outlet openings are linked to the line connectors so that in case of malfunctions during the treatment of a patient the complete exchange of the separator can be carried out within a very short time.

A fifth embodiment of a separator suitable for recovering solids from the solid-liquid mixture, with the suction air having been removed previously, is provided with:

i) a centrifuge housing having an inlet chamber, and a discharge channel, ii) a solid bowl centrifuge arranged in the centrifuge housing, said solid bowl centrifuge being provided with a bottom outlet vertically discharging by gravity solids and liquid residues after each working phase of the centrifuge, and with a top liquid outlet passing cleaned liquid into the discharge channel, iii) a connecting line having at least a first section and an end section and connecting the bottom outlet of the centrifuge with the inlet chamber of the centrifuge housing, the connecting line being provided with a collector bowl that forms a sedimentation chamber and a liquid residues collecting chamber, and iv) a feed back system for cycling liquid residues to the inlet chamber of the centrifuge housing.

This embodiment is particularly suited as a supplement to existing dental work stations, in which there is a clean air separator as described in DE-A- 27 13 321. This embodiment of the separator according to the invention is here used as a solids collector which is installed into the particular drain line.

For suction pumps which depend on the supply of a liquid-suction air mixture, a sixth embodiment of a separator to be inserted into the suction line, with an air-liquid mixture being conveyable in the suction line leading to the suction pump, is provided with:

i) a separator housing comprising
an air separating chamber designed as an upper part of the separator housing, the upper part having deflectors, an inlet for the mixture to be connected to the first section of the suction line, and an outlet for the separated clean air to be connected to the second section of the suction line,
a liquid collecting chamber arranged beneath the air separating chamber and having a drain opening, and
a sedimentation chamber for settling the solids up to a predetermined maximum settling level, the sedimentation chamber being provided in a collector bowl detachably mounted on the upper part of the separator housing, the upper edge of the collector bowl being above the drain opening;

ii) a drain line comprising
a first section extending upwardly in the separator housing and provided with the drain opening above the predetermined settling level of the solids, and
a liquid outlet being associated with the second section of the suction line; and iii) a discharge device arranged in the drain line and transferring separated liquid from the liquid collecting chamber to the second section of the suction line that leads to the suction pump.

In this arrangement a preferred embodiment provides that the liquid is sucked into the suction line by means of a venturi tube.

Figure 23:
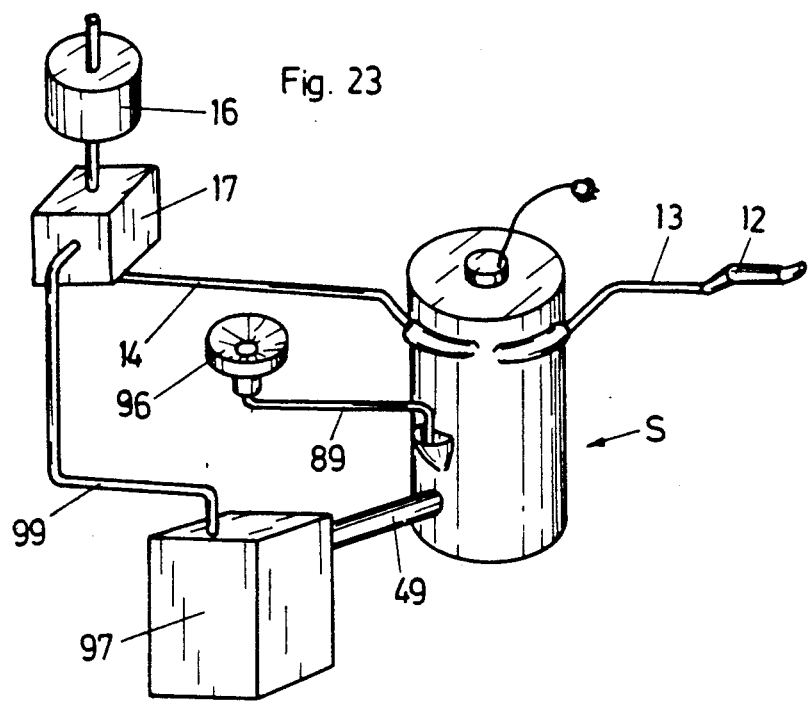
Figure 5:
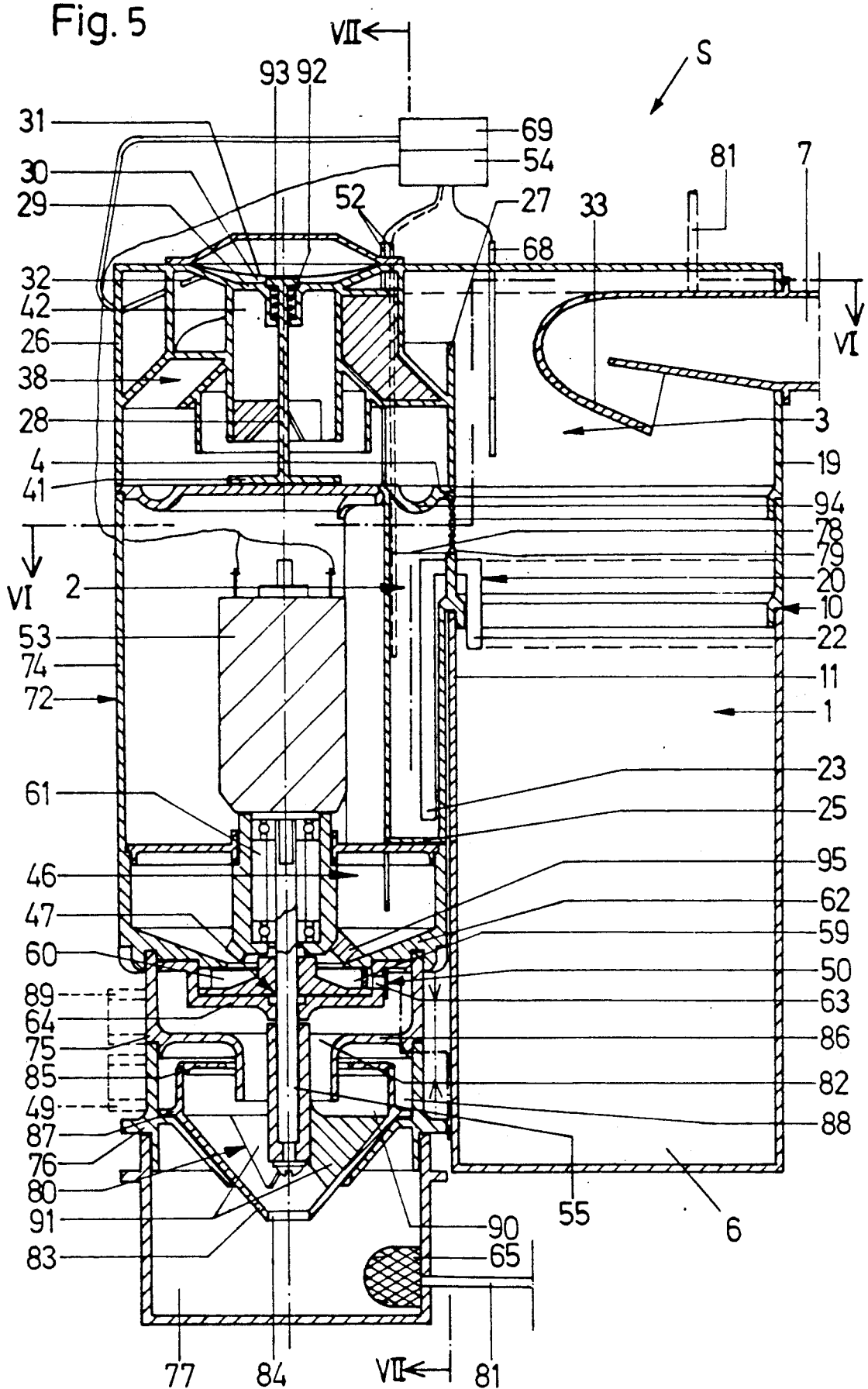
Figure 6:
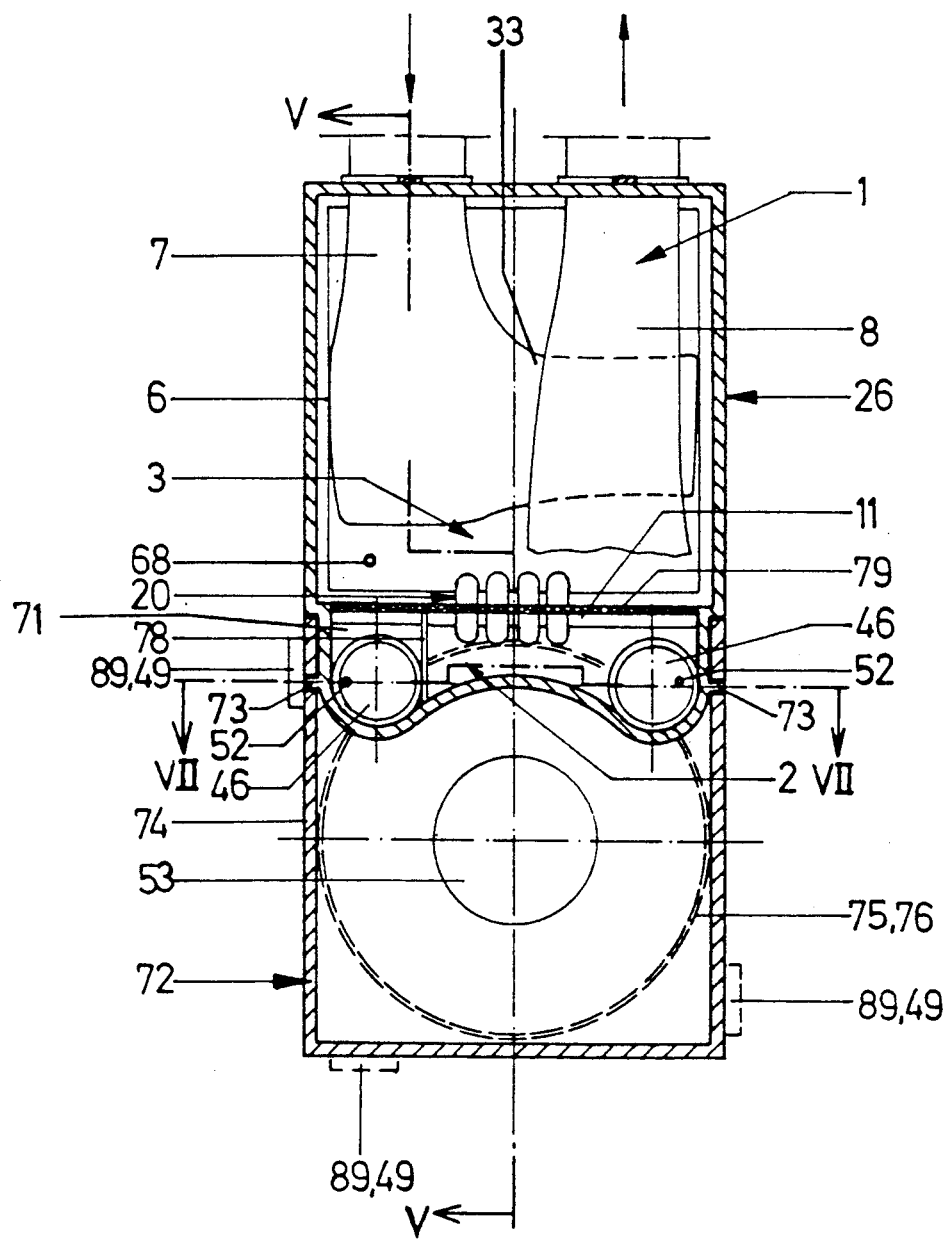
Figure 7:
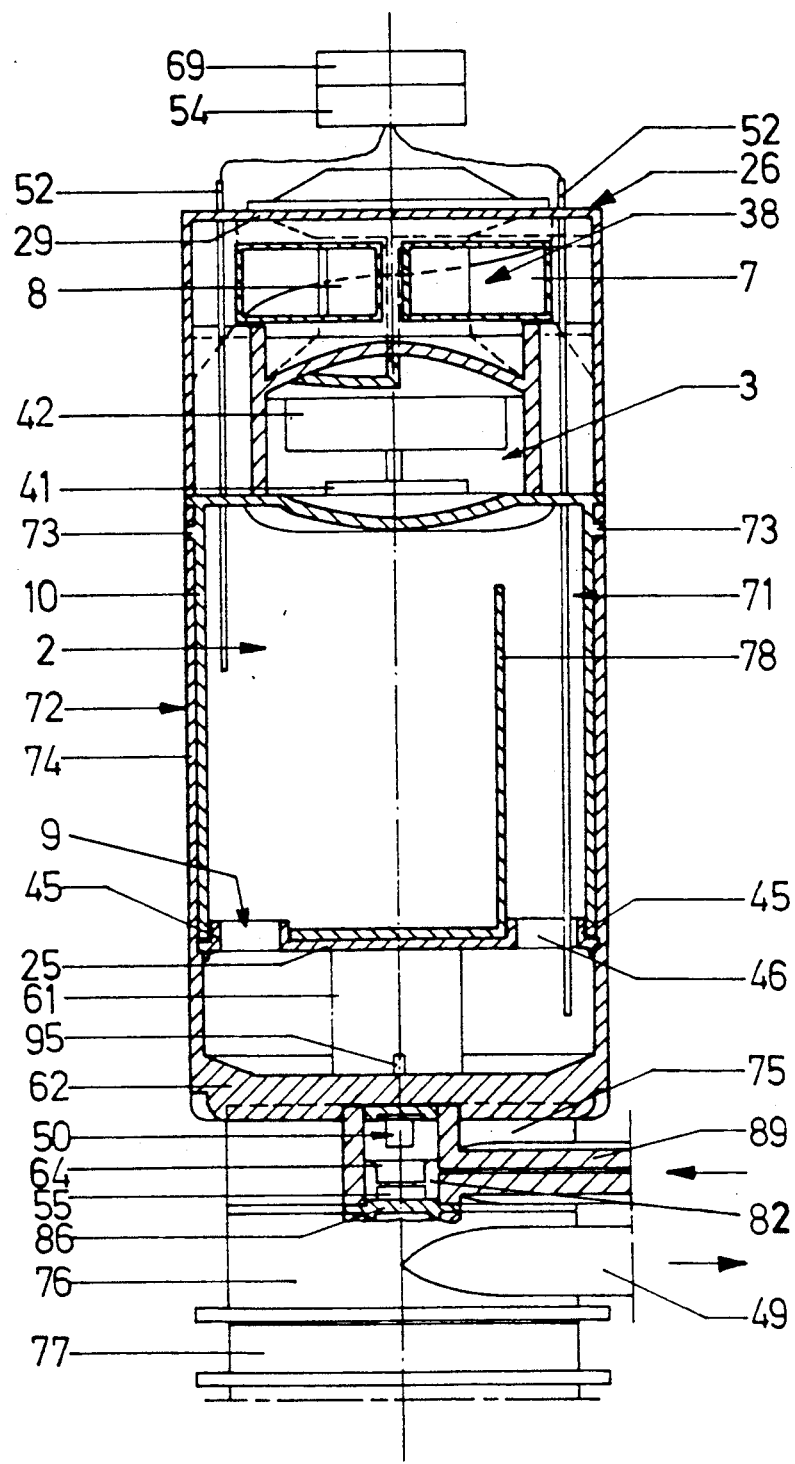
Figure 8:
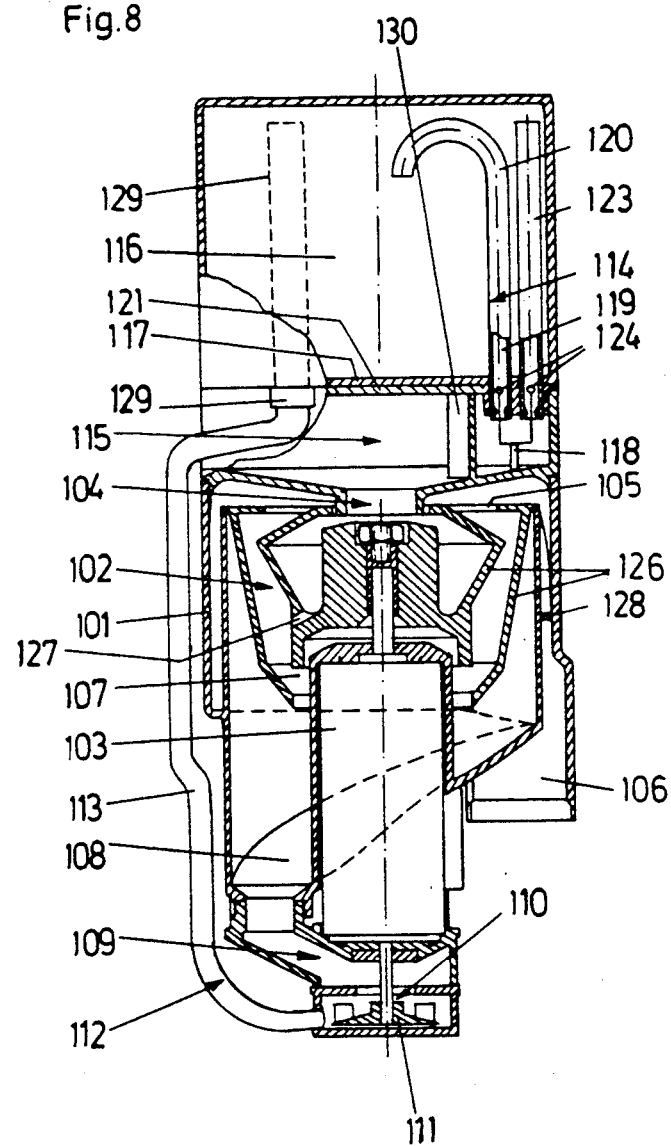
Figure 9:
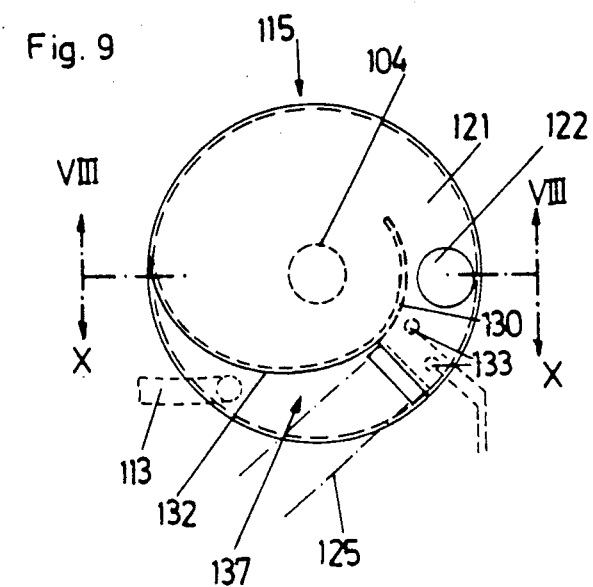
Figure 12:
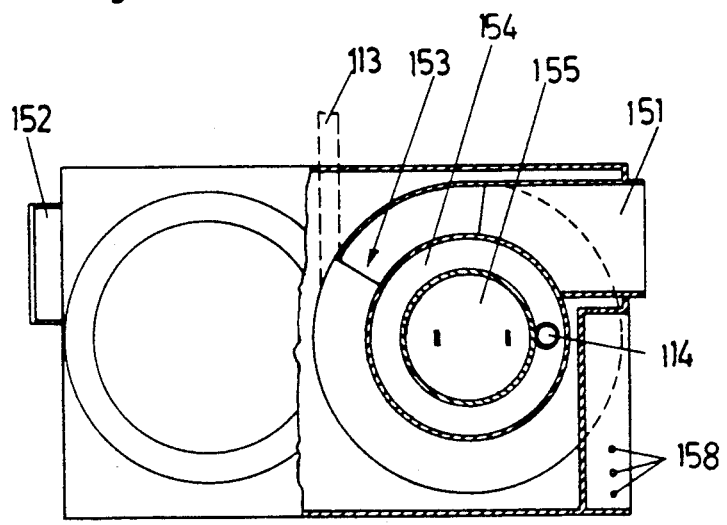
Figure 15:
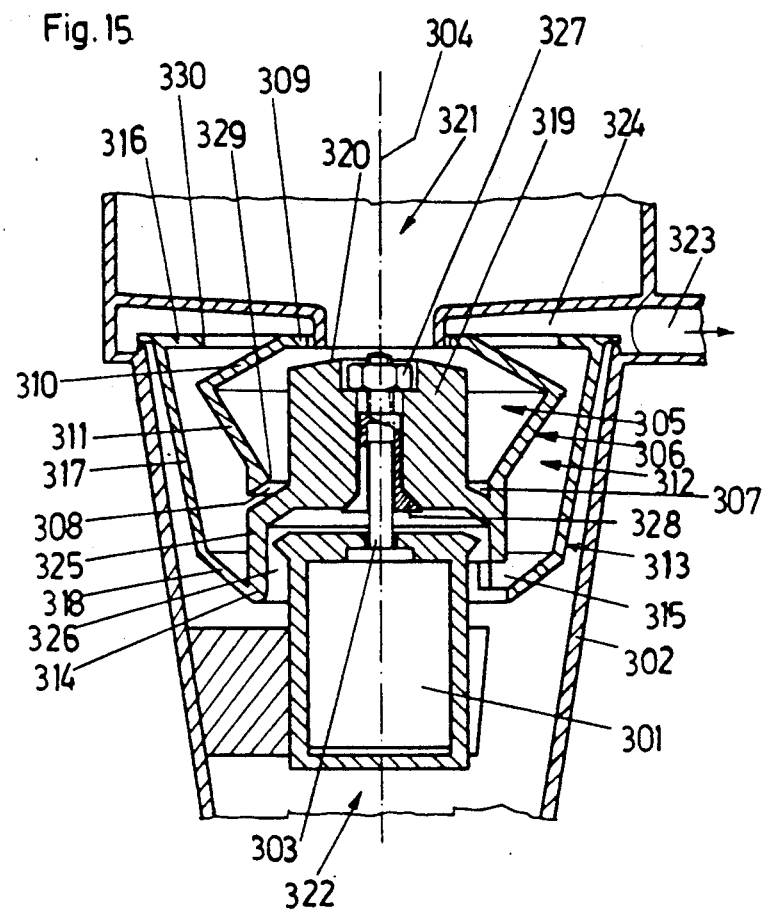
Figure 17:
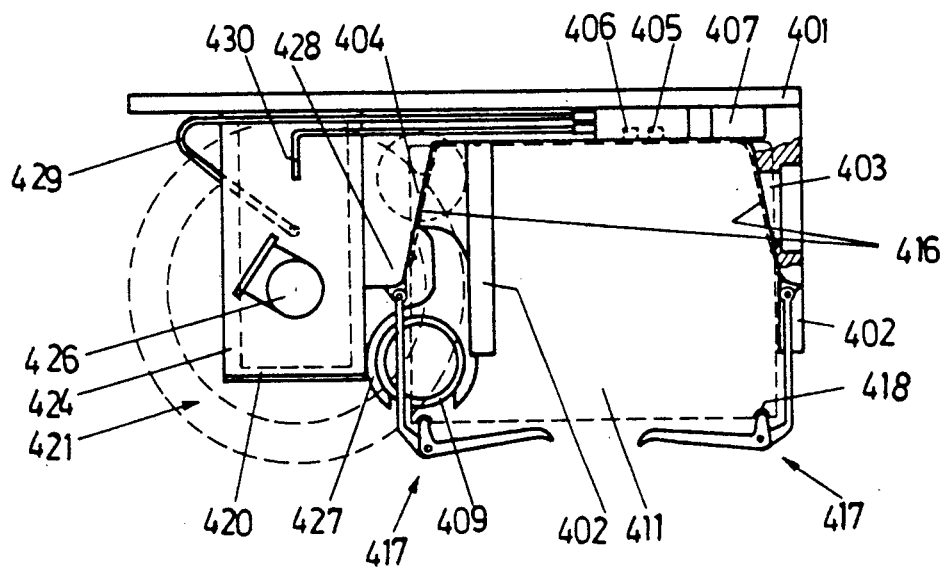
Figure 19:
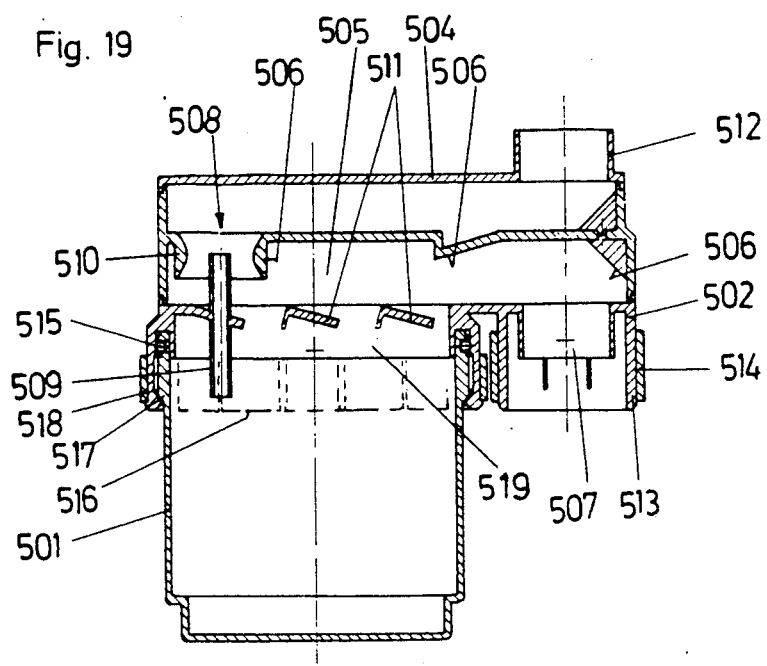
Figure 20:
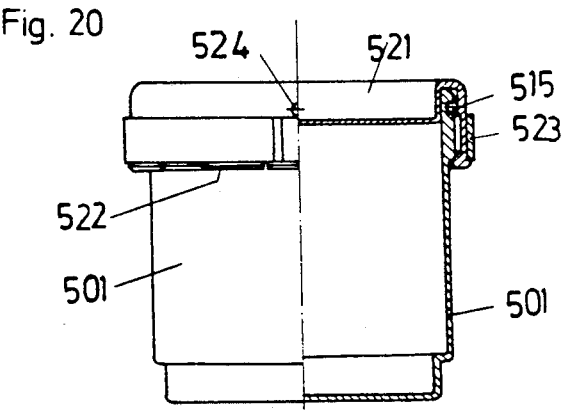
Figure 21:
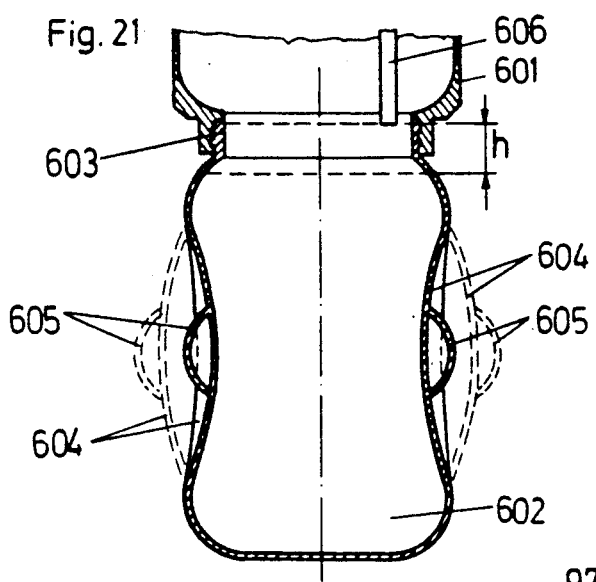
Figure 22:
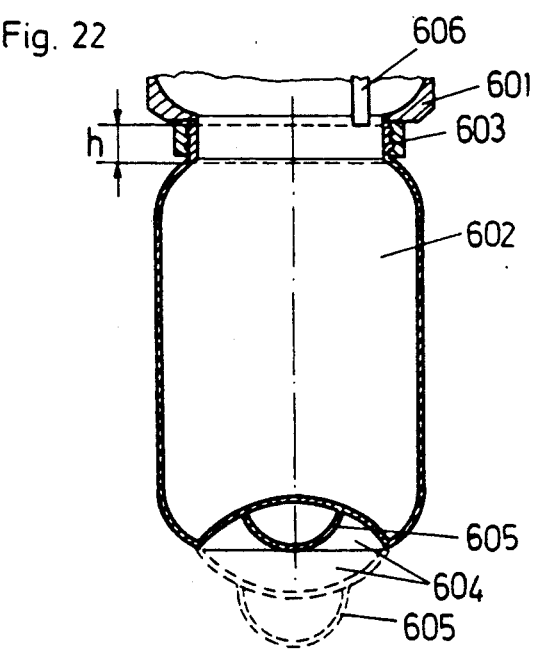
Figure 24:
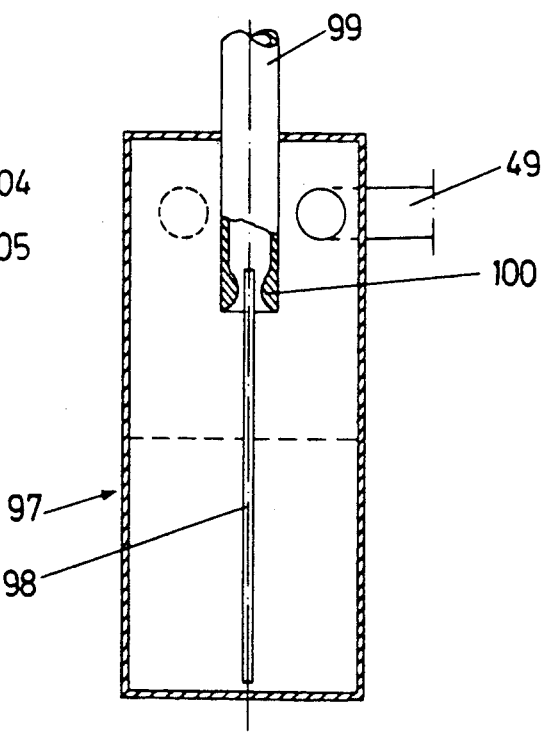
Figure 2:
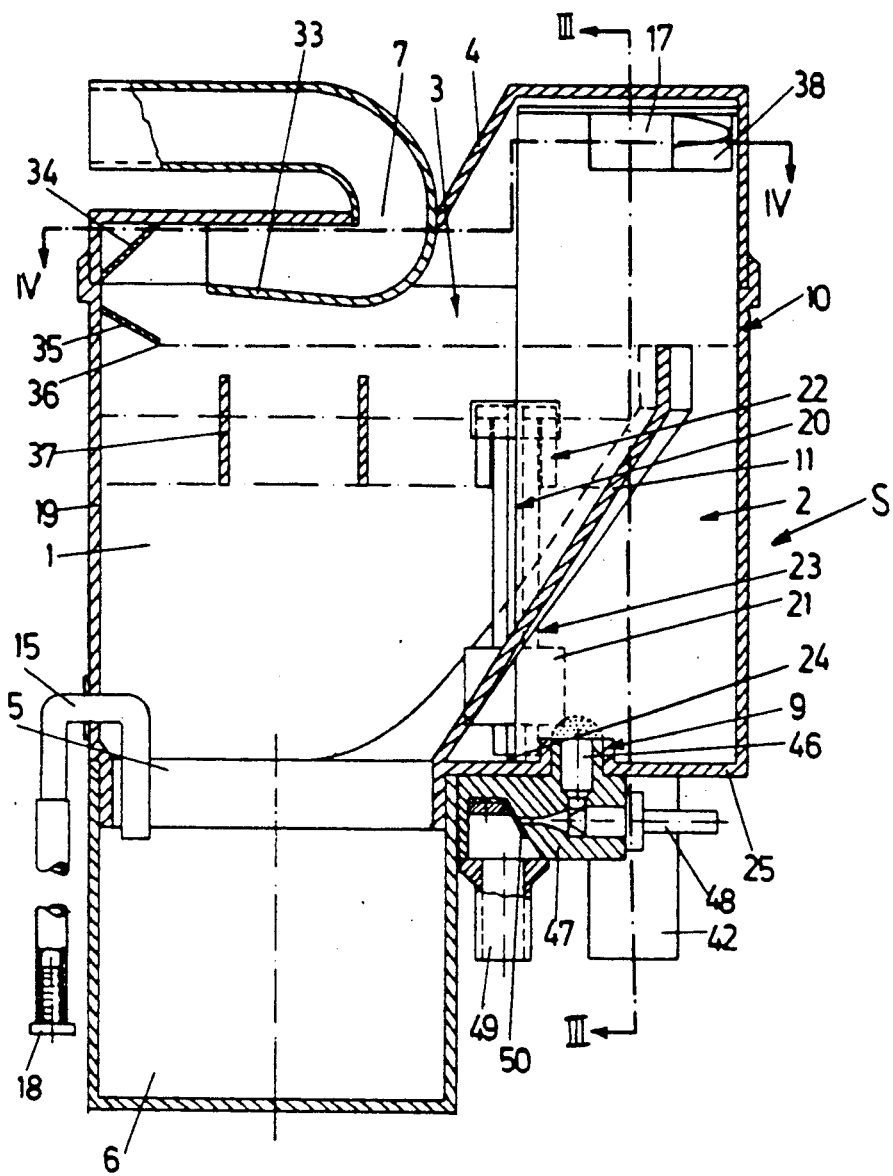
Figure 4:
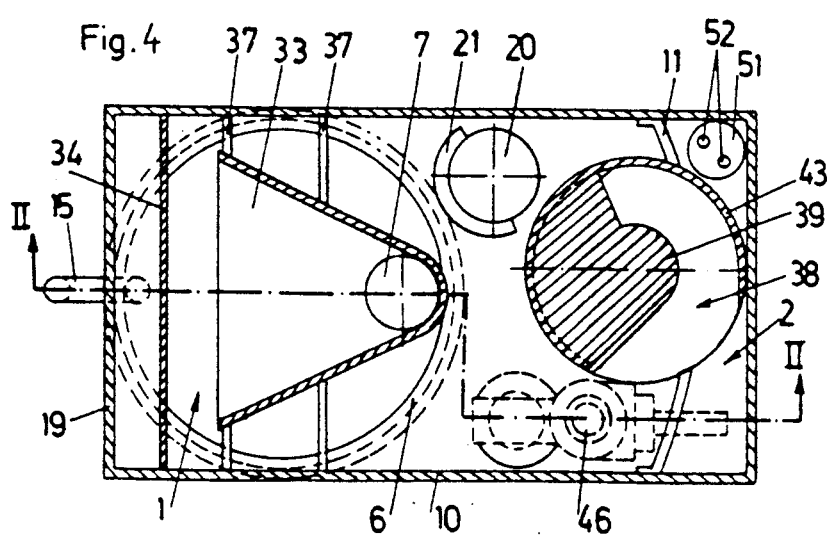

In the following the invention will be described in more detail with reference to the figures of the drawing without being limited thereto, in which FIG. 1 shows a diagrammatic view of a first embodiment of a dental suction unit, FIG. 2 is a vertical section of a first embodiment of a separator on the line II—II of FIG. 4, FIG. 3 is a vertical section of said first embodiment on the line III—III of FIG. 1, FIG. 4 is a horizontal section on the line IV—IV of FIG. 2, FIG. 5 is a vertical section of a second embodiment on the line V—V of FIG. 6, FIG. 6 is a horizontal section on the line VI—VI of FIG. 5, FIG. 7 is a vertical section on the line VII—VII of FIG. 5, FIG. 8 is a vertical section of a third embodiment on the line VIII—VIII of FIG. 9, FIG. 9 is a top view of the embodiment according to FIG. 8, with the sedimentation chamber being removed, and of the embodiments according to FIG. 10 or 11, FIG. 10 is a vertical view of a fourth embodiment on the Line X—X of FIG. 9, FIG. 11 is a vertical section of a fifth embodiment of a separator, FIG. 12 is a section on the line XII—XII of FIG. 11, FIG. 13 is a vertical section similar to FIG. 11 of a sixth embodiment of a separator, FIG. 14 is a vertical section similar to FIG. 13 of a seventh embodiment of a separator, FIG. 15 is an enlarged view of a vertical section of a centrifuge similar to FIGS. 8, 10, 11, 13 or 14, FIG. 16 is a front view of a support receiving a gravity separator and a centrifuge separator, FIG. 17 is a top view of the support of FIG. 16, FIG. 18 is a side view of the support of FIG. 16, FIG. 19 is a vertical section of an eighth embodiment of a separator, FIG. 20 is a partial longitudinal section of the closed collector bowl of FIG. 19, FIG. 21 is a longitudinal section of a second embodiment of a collector bowl, FIG. 22 is a longitudinal section of a third embodiment of a collector bowl, FIG. 23 is a diagrammatic view of a second embodiment of a dental suction unit, and FIG. 24 is a vertical section of a supplemental liquid collecting container according to FIG. 23.

FIGS. 1 and 23 show diagrammatic views of two different embodiments of dental systems for the discharge of the solids-liquid mixture produced in the patient's mouth during treatment. A system of this kind comprises a suction pump 16 to which a first section 13 and a second section 14 of a suction line leads, a suction handpiece of a suction nozzle 12 receiving the mixture being arranged at the end of said suction line. The mixture is through the first section 13 of the suction line conveyed to a separator S in which the mixture is separated. The clean air is through the second section 14 of the suction line discharged to the suction pump 16, the liquid leaves the separator S through the last section 49 of the drain line, and the solids settle in a collector bowl which is emptied from time to time. Without disturbance of the vacuum produced by the suction pump, it is possible in various embodiments to separate also a liquid-solids mixture which flows from a spittoon 96 via a drain line 89 into the separator S. While according to FIG. 1 solids-free liquid is discharged as drain water into the last section 49 of the drain line, FIG. 23 provides next to the end of the drain line a liquid collecting container 97 from which the liquid is via line 99 conveyed again to the second section 14 of the suction line. This is of advantage, when the suction system has a liquid-air separator 17, or is operated by a suction pump 16, e.g. a water ring pump, which requires a continuous liquid supply for sealing. As shown in FIG. 19, the liquid collecting container 97 together with line 99 may equally be arranged in the separator S so that a liquid-air mixture then enters into the second section 14 of the suction line.

A first embodiment of the separator S according to FIGS. 2 to 4 has a rectangular separator housing 10 which is divided into a sedimentation chamber 1 and into a secondary tank 2 by a partition 11, that ends at a distance from the housing cover 4. Above said chamber and said tank there is a common space that is part of an air separator chamber 3 that is formed in a cap 26. Above the sedimentation chamber 1 there is an inlet 7 for the mixture of solids, liquid and suction air coming from the dental suction nozzle 12, this inlet 7 being associated with a first deflector 33 so that the inlet is substantially U-shaped. The deflector 33 increases in width from the inlet 7 to the outer wall 19 of the housing 10. The sedimentation chamber 1 comprises a removable collector bowl 6 that is installed from below and held in sealing arrangement. The collector bowl 6 thus forms a sedimentation chamber above which a liquid collecting chamber forms.

By this deflection, swirling and impact against the outer wall 19 solids and liquid, which collect in the sedimentation chamber 1, are by means of the suction air separated from the mixture flowing through the inlet 7 and the deflector 33. The liquid collecting chamber of the sedimentation chamber also forms a stabilizing zone for the settling of the solids in the sedimentation chamber on the bottom of the collector bowl 6. As soon as the fluid reaches a predetermined level in the sedimentation chamber 1, the solid-liquid mixture, that continues to flow in, forces clarified liquid from the liquid collecting chamber over a liquid transfer system, that is arranged above the maximum level of the solid sediment and provided with a drain opening, into the secondary tank 2. Said liquid transfer system can be of any kind. A non-continuous transfer of liquid through the siphon 20 takes place according to FIGS. 2 to 4, the longer leg 23 of siphon 20 running close to the bottom into the secondary tank 2. The inlet opening of the shorter leg 22 lies in this arrangement above the maximum settling level and below the upper edge of the collector bowl 6, and the overflow level of the siphon 20 lies lower than the upper edge of the partition 11. The partition 11 substantially forms part of the outer surface of a truncated cone, which means a wall section of a funnel, through which the siphon 20 is vertically guided. In this connection, the longer leg 23 passes through the partition 11 and opens out close to the bottom of the secondary tank 2, where it lies on the bottom 25 on a stand-off piece 24. The deflector 33 increases in width from the inlet 7 to the outer wall 19 (FIG. 3), and additional deflectors 34, 35 are arranged obliquely in the corner area between the housing cover 4 and the outer wall 19, and the mixture coming from the first deflector 33 strikes these. The deflecting edge 36 of the third deflector 35 lies in the upper side of the partition 11.

Beneath the partition 11 the sedimentation chamber has a cylindrical section 15 on which the collector bowl 6 is removably fitted from below. An additional siphon 15 serves to remove the liquid contained in the sedimentation chamber 1 before the collector bowl 6 is removed, and is closed off by a plug 18 while the system is in use. Impact walls 37 are provided in the upper section of the sedimentation chamber 1, and these serve to calm the liquid. To this end, the inlet openings of the shorter leg 22 of the siphon 20 are level with the under side of the impact walls 37, and the overflow level of the siphon 20 is deeper than the upper side of the impact walls 37. In this connection, it is preferred that the siphon 20 consists of a plurality of pipes that are inserted collectively in a pipe support 21 in the partition wall 11.

The clean air outlet 8 is located in the air separator chamber 3 above the secondary tank 2. A cylinder 43 is arranged within the secondary tank 2, and this is connected through a passageway 44 close to the bottom with the secondary tank 2. Within the cylinder 43 the suction tube 42 runs centrally through the bottom 25, and its upper end constitutes the clean air outlet 8.

This is covered by an inverter dome 70, while leaving an annular gap. The suction tube 42 surrounds a float 41 that is a sealing cap, and this is drawn into an annular groove 57 in the inverter dome 70 when the liquid rises, and thus closes the clean air outlet 8. Above the inverter dome 70 there is the cyclone 38, so that the suction air passes from the air separator chamber 3 through a side air inlet opening 17 around the centre piece 39, upwards through an annular gap 56 between the inverter dome 70 and the cylinder 43, and is then deflected downwards once again within the inverter dome 70 and into the suction tube 42. Liquid that is deposited flows downwards over the deflectors 40, where it can drain into the secondary tank 2 through the opening 44.

The secondary tank 2 is emptied through the liquid outlet 9 in the pipe section 45 that rises above the bottom 25. This contains the suction channel 46 of a water jet injection pump that is provided as auxiliary pump 47, and covered over by a strainer. The non-return valve 50 is arranged on the outlet side of the water jet injection pump.

As can be seen in FIG. 3, within the secondary tank 2 a further chamber 51 is divided off and this is connected to the secondary tank at the side of the bottom; within this chamber, liquid level sensors 52 extend downwards from the housing cover 4. These can be configured in any way that is suitable for activating the control circuit for the solenoid valve that is incorporated in the water supply line 48. It is preferred that these sensors respond in accordance with the electrical conductivity of the liquid.

Between the sedimentation chamber 1 and the secondary tank 2 with the liquid outlet 9 that leads into the auxiliary pump 47, there can be at least one intermediate tank into which the siphon 20 opens, a second siphon 20 transferring the liquid that collects into the secondary tank 2. The intermediate tank could form an additional settling tank.

FIGS. 5 to 7 show a second embodiment of a separator S in which the auxiliary pump 47 is a vane-type impeller pump which is fitted to the liquid outlet 9 (FIG. 7) of the secondary tank 2, a solid bowl centrifuge 80 being arranged downstream of said vane-type impeller pump.

The housing 10 is again divided into a sedimentation chamber 1 and a secondary tank 2 by a partition 11, that ends at a distance from the housing cover 4. Above said chamber and said tank there is the air separator chamber 3 that is formed in a cap 26 of the housing 10. The inlet 7 is provided with a deflector 33 that increases in width from the inlet 7 to the outer wall 19 of the housing 10. The sedimentation chamber 1 comprises again a removable collector bowl 6 for the solids that is installed from below and held in sealing arrangement.

As soon as the fluid reaches a predetermined level in the sedimentation chamber 1, in this embodiment, too, the solid-liquid mixture, that continues to flow in, forces clarified liquid over a siphon 20, the longer leg 23 of which discharges close to the bottom in the secondary tank 2. The overflow level of the siphon 20 lies lower than the upper edge of the partition from which a mesh 79 extends upwards as far as the cover 4.

The air that has been cleared of solids and liquids is drawn upwards along a wall section 27 that extends as an extension of the partition 11 into the cap 26, downwards in a helical path of a cyclone 38 about a central suction tube 42, and then at the end of this upwards again through the suction tube 42, and finally through the clean air outlet 8 to the suction pump. The suction tube 42 is closeable by a sealing cap 41 that is installed on a rod 28 that extends centrally and upwards through the suction tube 42; this continues through the upper cover 29 of the cap 26 where it has a head 93, there being a compression spring 92 between the cover 29 and the head 93, so that the sealing cap 41 is forced into the closed position.

The upper cover 29 defines a chamber 30 in which there is a diaphragm 31, and which is at a partial vacuum through a line 32 that is connected to the clean air outlet 8. This means that the diaphragm 31 acts on the head 93 and keeps the sealing cap 41 in the open position. A valve 69 is incorporated in the line 32, this being operated by a control 54 that works in conjunction with liquid level sensor 68. When the level of the liquid in the housing 10 rises into the air separator chamber 3, the valve 69 is activated by the level sensor 68, and this connects the chamber 30 to the outside atmosphere, so that the sealing cap 41 closes the suction tube 42 under the force of the spring 92. It is advantageous that the suction pump is switched off automatically at the same time. A catch channel 94 around the cyclone separator 38 collects residual liquid and directs this into the housing 10, preferably into the secondary tank 2 that is located beneath this.

The suction channel 46 of an auxiliary pump 47 is incorporated in the pipe section 45 that rises above the bottom of the secondary tank, in this embodiment said auxiliary pump being a vane-type impeller pump arranged in a housing 72. This comprises an upper section 74 that contains the motor 53, the upper side of said upper section being aligned with the cover 4 and defining the cyclone 38 of the air separator chamber 3 below, a middle section 75 and a lower section 76. The drive shaft 55 that extends vertically is supported in a bearing assembly 61 that is arranged within the upper section 74, and this drive shaft bears the impeller 59 and, connected to this through supporting webs 91, a solid bowl centrifuge container 83. The bearing assembly 61 extends through a wider section of the suction channel 46 and is supported on a horizontal base plate 62 with a central opening 60 by means of supporting webs 95. An air line 71 leads from the wider section of the suction channel 46 back into the air separator chamber 3, this being separated from the secondary tank 2 by means of a partition 78. Beneath the opening 60 there is an impeller 59 that has curved vanes, which has an associated outlet opening 63 that can be closed off by a non-return valve 50, and seals off the inner chamber of the separator agains the ingress of unwanted air. The outlet opening 63 is arranged in an intermediate bottom 64 that separates the upper section 74 from the middle section 75; there is normal pressure beneath this intermediate bottom. The auxiliary pump 47 is controlled by the control unit 54, depending on the level of liquid in the suction channel 46 and in the secondary tank 2, this level being monitored by sensors 52.

The middle section 75 of the pump housing 72 contains a centrifuge inlet chamber 82, and is cylindrical, so that it can be rotated to any position. Drain line 89 (FIGS. 5,7) from the spittoon 96 opens out essentially tangentially into the centrifuge inlet chamber 82 that is defined below by a baffle 86 that extends horizontally in the peripheral portion and becomes a sleeve that is coaxial with the drive shaft 55 within the centrifuge inlet chamber 90, so that solids from the spittoon will be separated out by the centrifuge 80 that is formed in the subsequent lower section 76 of the pump housing. The centrifuge container 83 tapers towards the bottom to a base opening 84, through which the centrifuged solids pass into the trap 77 that is installed on the lower section 76. In contrast to this, the liquid rises within the centrifuge container 83 and passes through an annular flange 85 that protrudes inwards and into an outer annular channel 88 in the lower section 76, the annular channel being covered towards the trap 77 by an outer annular flange 87 of the centrifuge container 83. The liquid that has been cleared flows through the drain channel 49 which, like the drain line 89 from the spittoon can be rotated into any position. Since the trap 77 is in most instances of a limited capacity, which is smaller than the capacity of the collector bowl 6 of the sedimentation chamber 1, this trap 77 is connected by a line 81 to the mixture inlet 7, the inlet opening being covered by a strainer 65. The fine sludge that is mainly separated off in the centrifuge 80 is thus drawn back into the mixture inlet 7 by the suction pump 16 of the suction unit, a substantial portion of the solids settling in the sedimentation chamber 1, and a residual portion, which has possibly been sucked off with the liquid, being reconveyed to the centrifuge inlet chamber 82.

The separator housing 10 can be separated from the pump housing 74 very simply as soon as the cap 26 is removed. The two pipe sections 45 from slip-on fasteners for the secondary tank 2 that has side pins 73 that are insertable from above into slots in the side wall of the pump housing 72.

A third embodiment of a separator is shown in FIGS. 8 and 9. The separator has a housing 101 in which a solid bowl centrifuge 102 and a basin 109 arranged below the solid bowl centrifuge 102 are provided. The solid bowl centrifuge 102 is at the upper side provided with a central inlet 104 for a solid-liquid mixture which is to be separated and which has already been separated from the suction air. This may for example have been done by means of a conventional cyclone separator. The mixture passes over an inlet tube 125 (FIG. 9) and an inlet chamber 115 to the inlet 104. The centrifuge 102 has two solid side walls 126 which are arranged in series in flow direction and have convex generating lines defining, each, a centrifuge chamber. Gaps 127 are provided between the two centrifuge chambers, and the outer centrifuge chamber has a top liquid outlet 105 with a discharge channel 106 connected thereto.

The guide web 128 which rises steeply and follows a helical line is arranged in said discharge channel. Bottom outlets 107 of the solid outlet are formed at the lower side of the solid side wall 126 through which, when the centrifuge 102 is out of operation, the solids, which have been centrifuged off, flow together with some residual liquid through a funnel 108 into the basin 109. The funnel 108 is in this arrangement asymmetric and encloses the encapsulated driving motor 103 of the centrifuge 102.

In the embodiment according to FIG. 8 the lowest section of the basin 109 is formed by the pump housing 110 of a vane-type impeller pump or centrifugal pump 111, a first section 113 of a connecting line 112 leading from the pump housing 110 into the collector bowl 116 that is installed on the inlet chamber 115. The collector bowl 116 is an enclosed container and has in its interior an inlet tube 129, an outlet tube 119 of the second section 114 of the connecting line 112 and a vent tube 123, each rising from the bottom plate 117. The three tubes 129, 119 and 123 project from the bottom 117, the cover plate 121 of the inlet chamber 115 having an opening 122 through which the ends of the two tubes 119 and 123 project into the inlet chamber 115. In the interior of the ends of the two tubes 119 and 123 there are check valve devices 124 which are held by a common actuating lever 118, when the collector bowl is in the mounted position, and which close, when the collector bowl is being removed. The actuating lever 118 abuts on the bottom of the inlet chamber 115.

As can particularly be seen in FIG. 9, the inlet chamber 115 is substantially over one third of its circumference provided with a spirally inwardly guided outer wall section 132 so that an outer stepping 137 is provided in this region. In this region the inlet tube 129 projects from the bottom plate 117 of the collector bowl 116 into the open space, where the first connector of the first section 113 of the connecting line 112 lies.

The second section 114 of the connecting line 112 is formed by a syphon 120 the longer leg of which forms the outlet tube 119. In the extension of the outer wall section 132, a short partition 130 extends past opening 122 in the shape of a circular arc so that here an annular channel inlet elongates the inlet tube 129, and the liquid flows into said annular channel inlet via siphon 120. Measuring sensors 133 are arranged in this region by means of which the centrifuge 102 is activated, either when mixture is supplied through inlet tube 125 or when liquid is supplied through outlet tube 119. The pump 111 which is coupled to the centrifuge motor is activated simultaneously and transfers solids and residual liquid, respectively, which were discharged into basin 109 after the preceding centrifuging phase into the collector bowl 116 from which the syphon 120 passes the clarified liquid into the mixture inlet chamber 115 again, when the required filling level has been reached.

In a further embodiment according to FIG. 10, which has in respect of the solid bowl centrifuge 102 and the mixture inlet chamber 115 the same construction as the embodiment according to FIG. 8, the basin 109 is formed by the collector bowl 116 which is removably held at the lower side of the housing 101. In this arrangement, too, the pump 111 which comprises a vertically downwards extending intake tube 131 is arranged in the basin 109. The inlet opening of said intake tube is provided with a strainer and lies above a maximum sedimentation level of solids. Between the outlet of funnel 108 and the intake tube 131 a baffle 136 extends downwards. From the pressure side of the pump the connecting line 112, which comprises one section only in this embodiment, leads directly into the mixture inlet chamber 115 and is inserted in sealing arrangement into the cover plate 121 of said mixture inlet chamber by means of a ring 138 fitted into the opening 122. Solids from the centrifuge 102 fall into the collector bowl 116 from which the collected liquid is fed into the mixture inlet 104 of the centrifuge 102 by means of the pump 111. When the collector bowl 116 is removed, the filling level may be so high that the risk of spilling liquid occurs, and therefore the collector bowl 116 is provided with two wall regions 134 engaging in the collector bowl 116 and having a handle 135, each. Before the collector bowl is removed, the wall portions 134 are drawn outwards by means of the handles 135, thereby increasing the volume of the collector bowl 116 and lowering the liquid level to an extent which permits the removal of the collector bowl without any problems.

In the embodiment according to FIGS. 11 and 12, the separator S is similar to that in the embodiments according to FIGS. 2 to 4 and 5 to 7 and comprises an additional air separating device 149 so that a mixture of suction air, liquid and solids coming from a suction nozzle 12 can be separated into its components without prior separation of air. In such an embodiment, also the liquid-solids mixture from the spittoon 196 or from another additional dental device is fed into the mixture inlet chamber 115 via the inlet tube 125 which is connected to the drain line 89. The construction of the solid bowl centrifuge 102 together with basin 109, pump 111 and mixture inlet chamber 115 corresponds in this arrangement to the embodiment shown in FIG. 8, and therefore the parts which have already been described in detail and have the same reference numbers will not be described now.

The air separating device 149 comprises a mixture inlet 151 to which a cyclone separator 153 surrounding a central suction trunk 154 is connected. This leads via a valve device, which is not shown in detail, to an air outlet 152 and from there to the suction pump 16.

The solids-liquid mixture which has been separated from the air falls after the cyclone separator downwards into the sedimentation chamber 116, the collector bowl of which is removably held at the lower side of the air separating device 149 and comprises wall regions 134 which increase the volume to facilitate the removal of the collector bowl. By means of the pump 111 below the centrifuge 102 the collected solids-residual liquid mixture is pumped via the first section 113 of the connecting line 112 into the cyclone separator 153 and hence combines in the collector bowl 116 with the solids-liquid mixture which comes from the mixture inlet 151 and is separated in the cyclone separator 153.

The collected liquid and residual liquid contained in the liquid collecting chamber of the collector bowl 116 is now transferred into the mixture inlet chamber 115 by a second pump 150 via the second section 114 of the connecting line. To this end, the second pump 150 also has an intake tube 139 which projects vertically into the collector bowl 116. The drive shaft 141 of the second pump 150 is surrounded by a protecting tube 156 into which liquid will flow. This liquid will then be sprayed out again laterally through outlet openings 157 in the protecting tube 156 near the motor 155 and can be used for rinsing the lower wall sections of the air separator device 149. Thus the liquid rising into the protecting tube 156 is prevented from entering into the motor 155 which is often poorly sealed. Since there is a vacuum in the air separating device 149 a non-return valve 140 is provided at the outlet end of the connecting line 112 in the mixture inlet chamber 115, and if required the pump housing 110 can remain partly filled because of filling level sensors, which are not shown, so that here, too, the reflux of air is prevented. Since the amount of air which flows back hardly impairs the suction power it is not necessary to lock the first section 113 of the connecting line 112.

FIG. 12 shows a cross-sectional view of the air separating device in which measuring sensors 158 are shown, which are not visible in FIG. 11, by means of which the second pump 150, dependent on the filling level of the liquid collecting in the collector bowl or above the same, and a shut-off valve for the air outlet 152 are controlled.

In the embodiment according to FIG. 13, which also shows a combination of the separator S and an air separating device 149, the second pump 150 is arranged at the separator housing 101. Otherwise, the construction of the separator with the centrifuge 102 and the pump 109 arranged in the basin 109 corresponds again to the embodiments according to FIGS. 8 to 11. In this arrangement the second pump 105 is provided on the mixture inlet chamber 115, with an extension of the drive shaft of the motor 103 which extends upwards from the centrifuge 102 through the funnel-like mixture inlet 104 passing through the cover plate 121 of the mixture inlet chamber. The connecting line 112 comprises again a first section 113 which opens, like in the embodiment according to FIG. 11, into the cyclone separator, and a second section 114 between the collector bowl 116 and the mixture inlet chamber 115, the second section 114 comprising an extended intake tube 139 which starts at the liquid collecting chamber of the collector bowl and leads to the second pump 150. The suction trunk 154, above which the shut-off valve 159 of the air outlet 152 is provided, is centrally arranged in the air separating device 149 within the cyclone separator 153. Said shut-off valve comprises a diaphragm 160 which abuts the suction trunk 154 or rises therefrom depending on the pressure conditions at both sides of the diaphragm. Control is effected by means of the measuring sensors 158 which are shown in FIG. 12. Because of the vacuum in the air separating device 149 a non-return valve 140 is provided where the section 114 opens into the mixture inlet chamber 115. Pump 111 and the second pump 150 are coupled in respect of actuation so that, after each centrifuging phase, solids and residual liquid flowing off into the basin 109 are in the following centrifuging phase transferred into the collector bowl 116, with the residual liquid and liquid from the air separating device being reconveyed into the mixture inlet chamber 115 in each centrifuging phase. Control is effected either by the sensors 133 monitoring the supply of mixture from the spittoon 96 through the inlet tube 125 or by means of sensors in the collector bowl 116 which are not shown.

FIG. 14 shows a further embodiment similar to FIG. 13 in which the separator S also comprises an air separating device. In such an arrangement the mixture of liquid and solids from the spittoon 96 or from another dental device is also conveyed to the mixture inlet chamber 215 through the opening 225 of the drain line 89. The construction of the separator S and the solid bowl centrifuge 202 inclusive of the mixture inlet chamber 215 corresponds to the embodiments shown in FIGS. 8, 11 and 13 so that the parts with reference numbers between 201 and 208, between 226 and 228, further 234, 235, 252 as well as between 254 and 260 will not be described in further detail because they correspond to the parts described in detail in connection with FIGS. 8, 11 and 13 and having reference numbers between 101 and 108, between 126 and 128, further 134, 135, 152 as well as between 154 and 160.

By means of a pump 211 which is arranged below the centrifuge 202, liquid collected in the collector bowl 216 is sucked from the liquid collecting chamber via the first section 239 of the connecting line 212 and transferred into the mixture inlet chamber 215 via a second section 214. The pump 211 is actuated coaxially with the centrifuge 202 by a common motor 210 but can also have separate actuating means.

Since a vacuum is produced in the air separating chamber by means of the suction pump 16, a non-return valve 240 is provided at the outlet end of the section 214 of the drain line 212 into the mixture inlet chamber 215 so that here the reflux of air is prevented. Because of the liquid which is for the most part enclosed in the sections 239 and 214, the amount of air which flows back would hardly impair the suction power of the suction pump 16 so that the non-return valve 240 locking the section 215 of the drain line 212 is not absolutely necessary.

By means of the vacuum produced by the suction pump 16 in the air separating device 249, the solids together with the residual liquid which flow off into the basin 208 below the centrifuge 202 after each centrifuging phase are transferred via section 213 into the cyclone separator 253 so that they combine in the collector bowl 216 with the mixture of solids and liquid coming via the mixture inlet 251 and separated from the suction air in the cyclone separator 253. The residual liquid collecting above the settled solids is together with the liquid from the mixture inlet passed again into the mixture inlet chamber 215 by means of the pump 211. Control is effected again by means of sensors 233 monitoring a supply of mixture from the spittoon 96 through the drain line 89 which terminates in the opening 225, or by means of sensors in the collector bowl 216 which are not shown.

FIG. 15 shows in detail a longitudinal sectional view of the solid bowl centrifuge used in the embodiments according to FIGS. 8 to 14. This comprises a driving motor 301 having a vertically extending drive shaft 303 and being arranged a centrifuge housing 302. The drive shaft 303 carries a hub or core 319 of two centrifuge containers which are outwardly limited by two solid side walls 306,313 and have an axis of rotation 304. Via an inlet 321 which is centrally provided at the upper side, mixture of liquid and solids which is to be centrifuged passes into the first centrifuge container 305 in which a substantial part of the solids separates. The liquid which contains the residual solids exits from the first centrifuge container 305 through gaps 308 and flows into the second centrifuge chamber 312 in which the residual solids separate, the clarified liquid leaving the centrifuge housing 302 through the discharge channel 323. When the centrifuge is not in operation, the solids flow together with a liquid residue mainly from the second centrifuge container 312 through bottom outlets 315 to a collecting trunk or basin 322.

The two centrifuge containers 305 and 312 are limited by two solid side walls 306, 313 which are arranged in each other and have, each, a convex generating line comprising three straight sections. The first and inner centrifuge container 305 is hence separated from the outer centrifuge container 312 by a solid side wall 306, its generating line in its upper end section 309 extending radially and for the formation of the mixture inlet opening 321 at a distance from the axis of rotation 304, which means it lies in a radial plane. A central straight section 310 includes an angle of 150° and hence diverges obliquely downwards from the axis of rotation 304. The adjoining lower end section 311 of the generating line includes a right angle with the central section 310 and converges towards the axis of rotation 304, the lower end being spaced by a greater distance than the end of the upper end section 309. Hence, the lower end forms the overflow edge 329 of the solid side wall 306 in respect of the centrifuge container 312. Because of the connection to the core 319 the overflow edge 329 is divided into gaps 308. The solid side wall 306 extends slightly above the core 319, and the latter-mentioned has at its upper front side a bevelled ring area 320 which deflects the mixture to the central section 310 and accelerates the same. The pocket of the inner centrifuge container 305 formed by the sections 310 and 311 has a maximum radial extension, whereby particularly high centrifugal forces are obtained to which the liquid which exits at the lower side of the overflow edge 329 is far less exposed, however. There the liquid will therefore have a lower solids content between 5 and 15%. The gaps 308 are limited by connecting webs 304 which extend parallel to the axis of rotation 304 from the lower section of the solid side wall 306 to an extension 325 of the central section 319, the diameter of which is increased and corresponds to the lower section of the solid side wall 306 at the marginal edge 329. The webs 307 hence extend peripherally and not radially. The liquid exiting from the gaps 308 is accelerated by their nozzle effect and impinges on the solid side wall 313 of the outer centrifuge container 312 which has a similar construction. The generating line thereof also comprises three sections. The liquid coming from the inner centrifuge container 305 impinges on a straight central section 317 which diverges upwardly in respect of the axis of rotation 304 at an angle of 10°. The central section 317 extends to a height which is greater than the complete inner centrifuge container 304 because it projects downwardly over the centrifuge chamber 305 and the extension 325 of the central section 319. An upper end section 316 of the generating line extends from section 317 inwardly at an angle of 80° and hence lies in a radial plane and is preferably in alignment with the upper end section 309 of the inner solid side wall 306. Since it terminates at a great radial distance from the axis of rotation 304 an overflow edge 330 for the clarified liquid is formed, the solids transported from the inner centrifuge container 305, which are mainly fine particles, settling almost completely at the central portion 317 because of the higher centrifugal force.

To reduce height, a further straight section 318 of the generating line adjoins inwardly the central section 317 at an angle of 145° and hence approaches the axis of rotation 304 below 45°. The end of section 318 lies below the extension 325 of the central section 319, the distance to the axis of rotation 304 corresponding to the diameter of the extension 325. In the inoperative condition of the centrifuge, the solids outlet is positioned at the lowest point, the solids and mainly the residual liquid contained in the outer centrifuge container 312 moving downwards into the basin 322 under the effect of gravity. The connection between the solid side wall 313 and the central section 319 is formed by webs 314 which extend below the webs 307 and circumferentially staggered they extend peripherally and parallel to the axis upwards to the extension 325 so that the bottom outlet is formed by a ring of openings 315 which open from the outer centrifuge container 312 to the axis of rotation 304. To make this possible, the lower section of the extension 325 is configured as a sleeve which encloses an annular space 326 forming the top section of the basin 322. Probably because of the angle selected between the sections 310, 311 and 317, 318 of the two generating lines, the solids discharge completely so that further cleaning is not necessary. The annular space 326 is inside limited by the motor 301 which is arranged therein. When the centrifuge is in operation, liquid is allowed to exit through the openings 315 because these lie substantially nearer to the axis of rotation 304 than the upper overflow edge 330. Hence, the liquid lies in an annular channel 324 of the housing 302 which is formed above the overflow edge 330, said housing having a peripheral discharge channel 323.

The central section 319 has a bore which serves for the connection to the drive shaft 303 and in which a partly split clamping sleeve 328 with a thread arranged at its top is inserted. By turning the nut 327 abutting a recess in the front side of the central section 319, the clamping sleeve is pressed inwards at lower inclined faces and clamped to the drive shaft 303.

For greater mixture amounts to be separated, an enlargement of the centrifuge container is necessary, in which case the arrangement of a third and, if required, a fourth concentric solid side wall is easily possible.

The separators according to the invention are particularly suited for being installed in a chair for dental treatment, with a support being of advantage which permits quick removal of the complete separator S for cleaning and service purposes.

FIGS. 16 to 18 show views of a vertical support of this kind adapted to receive a gravity separator and a solid bowl centrifuge.

A support 401 according to FIG. 16 which is particularly suitable for mounting at a wall comprises a vertical support plate with projecting support members. The support 402 could obviously also be configured in a different way, for example be provided with a bottom plate to be positioned on a base etc. In the embodiment shown the support 401 serves to receive the separator housing 411 and a centrifuge housing 421, with a separation by gravity taking place in the housing 411, preferably with an air cyclone separator arranged ahead, and centrifugal separation taking place in the housing 421. This combination which is via a connector 426 (FIG. 17) also associated with the drain line 89 of the spittoon 96 yields particularly high separating rates of more than 99%. The support 401 may however only be provided for fastening one of the two housings 411,412. For the purpose of clarity the drawings show all parts of the support 401 in continuous lines, and the removable housings 411, 421 are restricted to the essential contours and shown in broken lines. For replacing or emptying the collector bowl 414 which is associated with the separator housing 411, the first-mentioned is not, as previously described, laterally removed from the separator as the only part but the complete housings 411 and 421 can be removed from the support so that maintenance and service operations of other parts, such as filling level sensors, electronic units for the control of pump or centrifuge motors or of clean air outlet sealings etc. can be carried out at suitable working places. Particularly in the case of such operations it is especially advantageous to remove the respective parts completely since replacement housings can be used in the meantime.

The support 401 adapted to receive the gravity separator housing 411 which comprises an upper part 412 and a collector bowl 414 has two horizontally projecting guide means 402 which are two C-shaped rails. The housing 411 the upper part 412 of which has lower guide rails 413 and the collector bowl 414 which has upper guide rails 415, each in the form of webs or ribs, can be inserted in said rails like a drawer. The guide means 413 and 415 complement each other to correspond to a space of the guide means 402 adapted to receive said complemented guide means 413 and 415 so that the guide means 402 also forms the connection between the upper part 412 and the collector bowl 414 which can additionally be fitted into one another by interpositioning a washer. Moreover, connectors 403 to 407 which lie free, when the housing 411 is removed, and are in alignment with corresponding inlet and outlet openings in the upper part 412, when the housing 411 is in the mounted position, are provided at the support 401. The mixture is supplied via the first line connector 403, the discharge of suction air, when an air cyclone separator is provided in the upper part 412, and the discharge of the air-liquid mixture are effected via the second line connector 404, both said connectors being arranged in the support 401. The tight connection with the inserted upper part 412 is obtained by snug fit surfaces 416 with washers 419 fitted therein, the necessary pressing being obtained by two catch means 417 which engage in notches 418 (FIG. 17) of the upper part 412 and which are fixed to the lateral webs 428. When the gravity separator also comprises a line for the separate suction of liquid, with the pump possibly being incorporated in the upper part 402 of the housing 411, an electric plug connector 407 and a third line connector 406 are provided at the support 401 and correspond with corresponding coupling elements at the housing 411.

A further plug connector 405 is provided according to the illustrated embodiment through which sludge separated by means of the centrifuge is reconveyed into the gravity separator housing 411.

For removably fastening the housing 421 which contains a centrifuge, there are provided a lower support plate 420, connectors 408, 490, 410 and elastic sleeves 422, 423. The housing 421 has a smallest possible support surface on the lower side which may be provided at the bottom of an individual basin or at the bottom of a pump 425. The support plate 420 may in the case of a pump 425 again be provided with an electric plug connector 410 and a sixth line connector for the sludge to be discharged. From there a connecting line 429 leads back to the seventh line connector 405 through which the sludge is reconveyed to the collector bowl 414 of the housing 411.

For the sole use of the housing 421 with centrifuge, a collector bowl can, as already mentioned, be configured as lower part so that the connecting line 429 is not provided.

The housing 421 which stands on the support plate 420 is at the upper side connected to the coaxial fourth connector 408, through which the mixture to be separated moves directly from the suction nozzle 12, or via the drain line 430 from a gravity separator, or via the connector 426 from the spittoon 96 into the housing 421, the sleeve 422 forming an elastic easily releasable line connection and holding connection for the housing 421. A line connector for the last section of drain line 49 is associated with the lateral outlet for the clarified liquid at a fork-like socket 427 of the support 401, an elastic, easily releasable sleeve 423 forming the connection. Hence, the housing 421 can be completely removed towards the upper side, the "tip mounting" of the housing 421 permitting a particular quiet running of the centrifuge. The support 401 is further provided with means receiving a sieve drawer 424 which is arranged ahead of the fourth line connector 408 to prevent greater particles, particularly those coming from the spittoon 96, from entering into the centrifuge.

Depending on the construction of the separator, the connectors 403 to 407 and 408 to 410 can be adapted to the device used and configured in a suitable manner. The seventh and third line connectors 405, 406 as well as the seventh line connector for the connecting line 429 may also be provided with snug fit surfaces, and the first and second line connectors 403 and 404 can be provided as plug-in connectors.

FIGS. 19 and 20 show a further embodiment of a separator which separates only the solids from a mixture of suction air, solids and liquid and, according to the installation shown in FIG. 23, admixes the liquid again to the suction air, the liquid being separated from the suction air in an individual liquid-air separator 17. A separator of this kind is hence particularly suited as a supplement of installations which are already in operation and already provided with a liquid-air separator.

The separator has according to FIG. 19 a separator housing which comprises a collector bowl 501 with an outwardly thickened upper edge, a central housing section 502 and an upper housing section 504. The central housing section 502 comprises the air separating chamber 505 which is open towards the collector bowl 501. A hood overlapping the edge 515 is formed at the central housing section 502 which has adjoining thereto a connecting piece 513 as a mixture inlet 507 for a first section 13 of the suction line coming from the suction nozzle 12. Said first section is fixed by means of a securing ring 514. The hood which fixes the collector bowl 501 has at its circumference a number of resilient tongues 516 which are enclosed by a collar 518. The tongues 516 terminate in inwardly directed projections 517 which engage below the thickened edge 515 of the collector bowl. The ring 518 is vertically displaceable, and in the upper end position radial spreading of the tongues 516 is possible so that the collector bowl 501 which is sealingly incorporated by means of an 0-ring can be removed. When the ring 518 is in the lower end position, radial spreading of the tongues 516 is not possible. In this locking position, the ring 518 is rotatable but after rotation secured against upward movement by means of a projection (not shown) of the central housing section 502.

The separating chamber 505 has next to the inlet 507 which extends parallel to the collector bowl 501 a first deflection by 90°, the smallest passage cross-section being given here by an additional inclined surface 506. From there the separating chamber 505 widens so that the suction air has to discharge the liquid-solids mixture which it transports because of the high flow loss. The space above the collector bowl 501 is divided by transversal, substantially L-shaped cross bars 511 which direct the suction air upwards to the air outlet 508 while they allow the liquid-solids mixture to flow downwards through an air-calmed zone 519 into the collector bowl 501. Air deflecting surfaces 506 which produce additional turbulences are provided, the air deflecting surface which is farest away from the inlet 507 being the external surface of a pipe socket which projects downwards from the central housing section 502 and forms outlet 508. The pipe socket is a venturi tube 510 because of its throat portion into which an intake tube 509 projects. This is held in a cross bar and projects with its lower end into the upper part of the collector bowl 501. The liquid which collects in the collector bowl 501 above the settled solids is superficially sucked off by the intake tube 509 and remixed with the suction air in the outlet 508. Because of the calmed zone 519 below the cross bars 511 which are slightly inclined, the surface of the liquid to be sucked off is also calm and hence free of solids. The position of the lower edge of the intake tube 509 is selected in such a way that the collector bowl 501 to be emptied can easily be removed and lies substantially at the height of the inwardly extending projections 517 of the tongues 516.

The mixture of liquid and suction air which is discharged through the outlet 508 and now free of solid is passed through a channel which is covered by the upper part 504 of the housing to a connecting piece 512 which is preferably but not necessarily an extension of connecting piece 507. The mixture of liquid and suction air which is sucked off through the connecting piece 512 is passed into an external liquid-air separator 17 which is provided anyhow in dental suction installations.

FIG. 20 shows the removed collector bowl 501 comprising a cover 521 for the transport. Said cover 521 corresponds in this arrangement to the hood of the central section 502 of the housing, which means that its edge is also provided with radially extensible tongues 522 which are surrounded by a vertically displaceable collar 523 and lockable. A nose 524 can be seen in that part which is not shown in cross section, said nose securing the ring 523 which is in its lowest position against being pushed upwards unintentionally.

Four different collector bowls have been described in the embodiments disclosed so far. The collector bowl shown in FIGS. 10 to 14 will now be described in detail with reference to FIGS. 21 and 22. The collector bowl 602 is removably fastened to the housing 601 of the separator and for example at its upper edge provided with a thread which is screwable into the opening of the housing. From the collecting mixture of solids and liquid, the solids settle in the collector bowl 602, while the liquid is sucked off again. The intake tube 606, which is shown schematically only, serves for this purpose, and its inlet opening defines the filling height and is arranged at the highest possible point so that the greatest possible filling amount is obtained. The inlet opening of the intake tube 606 lies for example, as shown, substantially at the height of edge 603 of the collector bowl so that the latter-mentioned is always filled up to its edge.

The collector bowl 602 comprises at least one wall region 604 the position of which can be changed. When the collector bowl 602 is fastened to the housing 601, each wall region 604 projects inwardly into the collector bowl 602, as shown by continuous lines. If the collector bowl 602 which is filled up to its edge shall now be emptied or exchanged, each wall region 604 is pulled outwards by means of handles 605 which are arranged at the outer side so that it is moved into the position illustrated by broken lines. The volume increase of the collector bowl 602 which is obtained thereby effects lowering of the contents by the height h, which corresponds in the illustrated embodiments to substantially a tenth of the total height. Because of the empty space in the region adjoining the edge, the collector bowl 602 can easily be removed from the housing 601 and emptied or closed by means of a cover and replaced by an empty collector bowl.

As shown in FIG. 21, two movable wall regions 604 are provided at the side wall of the collector bowl, and FIG. 22 shows an embodiment in which the wall region 604 is formed at the bottom wall. Several wall regions 604 are obviously possible, for example at the bottom wall and at the side wall of the collector bowl. Each handle 605 is preferably dimensioned in such a way that it lies in the inwardly projecting position of the wall region 604, within the superficial area of the collector bowl.

As already mentioned, installations which are already in operation may be provided with a liquid-air separator 17 which is associated with the suction pump 16. The suction pump 16 may also be a water ring pump or the like which requires a continuous liquid supply for sealing. The installation shown in FIG. 23 comprises a liquid-air separator 17 in the second section 14 of the suction line which reconveys liquid separated in the separator 5 and exiting through the drain line 49 to the suction air. In the embodiment according to FIG. 19, the drain line is formed by the intake tube 509 and integrated into housing section 503. In all other embodiments the separator S can be supplemented by a liquid collecting chamber 97 which is schematically shown in FIG. 23 and connected to the drain line. This has already been shown in FIGS. 11, 13 and 14 by the dot-dash lines.

FIG. 24 shows a sectional view of the liquid collecting container 97 from which the collecting liquid is reconveyed to the flow of clean air. This illustration has been restricted to the essential features. The end of line 99 which lies in the container 97 forms the inlet opening of a venturi nozzle 100 in which the end of an intake line 98 for the liquid is arranged which extends almost to the bottom of container 97. The lower end of intake line 98 forms the inlet for the clarified liquid which is conveyed to the container 97 through drain line 49. In the upper part of the container 97, there may be provided an additional air compensating opening or overflow opening which is shown in broken lines.

We claim:

1. A separator for separating a mixture of solids, liquids and suction air, to be inserted into a suction line of a dental system, so that the suction line is divided into two sections, the first section being provided with a suction nozzle discharging the mixture out of the mouth of a patient, and the second section leading to a suction pump, said separator comprising:
  i) a separator housing comprising
    an upper air separating chamber having deflectors, an inlet for the mixture to be connected to the first section of the suction line, and an outlet for the separated clean air to be connected to the second section of the suction line,
    an intermediate liquid collecting chamber having a drain opening,
    a lower sedimentation chamber for settling the solids up to a predetermined maximum settling level, and
    a detachable collector bowl embodying the sedimentation chamber, the upper edge of the collector bowl being above the drain opening;
  ii) a drain line between the liquid collecting chamber and a liquid outlet at the end of the drain line, said drain line comprising
    several sections, a first section extending upwardly in the liquid collecting chamber, being provided with the drain opening above the predetermined settling level of the solids, and being submersible by accumulated liquid up to a predetermined maximum flood level, and
    a non-return valve means being arranged in a further section of the drain line and securing against an ingress of unwanted air into the separator housing; and
  iii) a drain system integrated within the drain line, said system discharging liquid that is accumulated up to the predetermined flood level out of the liquid collecting chamber and transferring said liquid to the liquid outlet.

2. A separator as in claim 1, wherein said drain system integrated within the drain line comprises a pump means, the non-return valve means being associated with the pressure side of the pump means.

3. A separator as in claim 2, wherein said pump means is arranged within the upwardly extending first section of the drain line.

4. A separator as in claim 3, wherein said pump means comprises an electric vane-type impeller pump.

5. A separator as in claim 4, wherein said pump means is actuated by sensors arranged in the liquid collecting chamber and defining a low level corresponding to the position of the drain opening as well as a peak level equal to the predetermined flood level.

6. A separator as in claim 1, wherein said separator housing further comprises a secondary tank representing an intermediate section of the drain line, said secondary tank being associated with the liquid collecting chamber and being open into the air separating chamber, a liquid transfer system including the first section of the drain line, being arranged between the liquid collecting chamber and the secondary tank.

7. A separator as in claim 6, wherein said liquid transfer system comprises a syphon having an intake leg and an overflow level equal to said flood level of the first section of the drain line, said first section forming the intake leg of the syphon.

8. A separator as in claim 6, wherein said secondary tank comprises a pump housing containing a pump means, said non-return valve means being arranged at the outlet of the pump housing.

9. A separator as in claim 8, wherein said pump means comprises an electric vane-type impeller pump.

10. A separator as in claim 6, wherein said separator housing further comprises a housing cover and a partition that ends at a distance from the housing cover and separates the secondary tank from the liquid collecting chamber, the liquid transfer system being arranged in the partition.

11. A separator as in claim 10, wherein said liquid transfer system comprises a syphon having an intake leg and an overflow level equal to said flood level of the first section of the drain line, said first section forming the intake leg of the syphon, and wherein the syphon is inserted into the partition, the overflow level of the syphon lying beneath the upper edge of the partition.

12. A separator as in claim 10, wherein said secondary tank comprises a pump housing containing a pump means, said non-return valve means being arranged at the outlet of the pump housing.

13. A separator as in claim 12, wherein said pump means comprises an electric vane-type impeller pump.

14. A separator as in claim 1, wherein said air separating chamber has deflectors and a cyclone arrangement that has a helical path being formed in the air separating chamber, the outlet for separated clean air which includes a suction trunk being centrally arranged within the helical path and being closable by an axially guided sealing member.

15. A separator as in claim 1, further comprising: a liquid collecting container connected to the liquid outlet at the end of the drain line, and a liquid discharge device transferring liquid from the liquid collecting container to the second section of the suction line that leads to the suction pump to which a separator for liquids and suction air is associated, the liquid discharge device comprising a venturi tube arrangement having a downstream end located in the second section of the suction line.

16. A separator for separating a mixture of solids, liquids and suction air, to be inserted into a suction line of a dental system so that the suction line is divided into two sections, the first section being provided with a suction nozzle discharging the mixture out of the mouth of a patient, and the second section leading to a suction pump, said separator comprising:
 i) a separator housing comprising
  an upper air separating chamber having deflectors, an inlet for the mixture to be connected to the first section of the suction line, and an outlet for the separated clean air to be connected to the second section of the suction line,
  an intermediate liquid collecting chamber having a drain opening,
  a lower sedimentation chamber for settling the solids up to a predetermined maximum settling level, and
  a detachable collector bowl embodying the sedimentation chamber, the upper edge of the collector bowl being above the drain opening;
 ii) a drain line between the liquid collecting chamber and a liquid outlet at the end of the drain line, said drain line comprising
  several sections, a first section being arranged in the liquid collecting chamber and provided with the drain opening above the predetermined settling level of the solids, said drain opening being submersible by accumulated liquid up to a predetermined maximum flood level,
  a non-return valve means being arranged in a further section of the drain line and securing against an ingress of unwanted air into the separator housing, and
  a last section, a centrifuge housing being inserted into the last section of the drain line and having an inlet chamber and a discharge channel terminating at the liquid outlet, the non-return valve means being arranged between the first and the last section of the drain line;
 iii) a pump means arranged in the drain line, said pump means discharging liquid that is accumulated up to the predetermined flood level out of the liquid collecting chamber and transferring said liquid to the inlet chamber of the centrifuge housing; and
 iv) a solid bowl centrifuge arranged in centrifuge housing, said solid bowl centrifuge being provided with a bottom outlet vertically discharging by gravity solids and liquid residues after each working phase of the centrifuge, and with a top liquid outlet passing cleaned liquid into the discharge channel.

17. A separator as in claim 16, wherein said pump means is arranged within the upwardly extending first section of the drain line.

18. A separator as in claim 17, wherein said pump means comprises an electric vane-type impeller pump.

19. A separator as in claim 18, wherein said pump means is actuated by sensors arranged in the liquid collecting chamber and defining a low level corresponding to the position of the drain opening as well as a peak level equal to the predetermined flood level.

20. A separator as in claim 16, wherein said pump means comprises an electric vane-type impeller pump arranged in a pump housing representing an intermediate section of the drain line and having a downstream opening, the non-return valve means being arranged at the downstream opening of the pump housing.

21. A separator as in claim 20, wherein said downstream opening opens into the inlet chamber of the centrifuge housing.

22. A separator as in claim 21, wherein said inlet chamber of the centrifuge housing tapers downwardly and terminates at an annular sleeve axially protruding into the solid bowl centrifuge.

23. A separator as in claim 22, wherein said solid bowl centrifuge comprises an outer side having an annular flange, an annular channel being defined by the annular sleeve, the annular flange, and the centrifuge housing, the discharge channel being connected to the annular channel.

24. A separator as in claim 20, wherein said vane-type impeller pump and said solid bowl centrifuge are arranged on a common drive shaft.

25. A separator as in claim 16, further comprising a feed-back system for cycling liquid residues that are discharged by gravity out of the bottom outlet of the solid bowl centrifuge to the inlet chamber of the centrifuge housing.

26. A separator as in claim 25, wherein said feed-back system comprises a basin for receiving the liquid residues and a connecting line starting from the basin and having an end section terminating at the inlet chamber of the centrifuge housing.

27. A separator as in claim 26, wherein said basin comprises a collector bowl for settling solids, said collector bowl being held detachably on the centrifuge housing.

28. A separator as in claim 26, wherein said feed-back system comprises a pump means that has an intake tube forming a first section of the connecting line and having an intake opening above a predetermined maximum settling level of the collector bowl, the end section terminating at the inlet chamber of the centrifuge housing and starting from the pressure side of the pump means.

29. A separator as in claim 28, wherein said pump means comprises an electric vane-type impeller pump.

30. A separator as in claim 26, wherein said connecting line starting from the basin comprises a first section leading to a collector bowl that forms a sedimentation chamber and a liquid collecting chamber, and a further section starting from the liquid collecting chamber, said further section including the end section terminating at the inlet chamber of the centrifuge housing, and further comprises a pump means transferring the solids and the liquid residues into the collector bowl.

31. A separator as in claim 30, wherein said collector bowl is the detachable collector bowl of the separator housing, and wherein said further section of the connecting line is formed by at least one section of the drain line.

32. A separator as in claim 30, wherein said pump means transferring the solids and the liquid residues into the collector bowl of the separator housing is formed by the suction pump of the dental system.

33. A separator as in claim 26, wherein said basin forms a pump housing arranged on the centrifuge housing, the connecting line starting from the pump housing in which a pump means is arranged.

34. A separator as in claim 33, wherein said pump means comprises an electric vane-type impeller pump.

35. A separator as in claim 33, wherein said connecting line starting from the pump housing comprises a first section leading to a collector bowl that forms a sedimentation chamber and a liquid collecting chamber, and a further section starting from the liquid collecting chamber, said further section including the end section terminating at the inlet chamber of the centrifuge housing.

36. A separator as in claim 35, wherein said collector bowl is the detachable collector bowl of the separator housing, and wherein said further section of the connecting line is formed by at least one section of the drain line.

37. A separator as in claim 16, wherein said solid bowl centrifuge comprises at least two centrifuge chambers being serially arranged in the drain line and being arranged on a common drive shaft in the centrifuge housing, each centrifuge chamber comprising a solid side wall having a convex line generated by rotation about an axis.

38. A separator as in claim 37, wherein said solid bowl centrifuge comprises two centrifuge chambers formed by single centrifuge containers, said centrifuge containers being arranged in each other.

39. A separator as in claim 38, wherein each centrifuge container comprises a solid side wall held on a core common to both centrifuge containers by connecting webs defining gaps, the webs of the inner centrifuge container being arranged at the bottom part of the side wall of the inner centrifuge container and the respective gaps forming downwardly inclined openings for liquid and solids penetrating into the outer centrifuge container, the common core including a sleeve mountable on a drive shaft that is rotatably supported by the centrifuge housing.

40. A separator as in claim 39, wherein said core comprises an extension downwardly protruding the inner centrifuge container and having an enlarged diameter, the connecting webs downwardly extending between the bottom part of the side wall and the extension of the core.

41. A separator as in claim 40, wherein said downwardly protruding extension forms a sleeve, and the webs of the outer centrifuge container extend upwardly between a bottom part of the side wall of the outer centrifuge container and the extension of the core, the respective gaps forming openings for penetration of solids into the interior of the sleeve.

42. A separator as in claim 39, wherein the side wall of said inner centrifuge container upwardly protrudes the core and defines a central opening, and wherein the annular sleeve of the downwardly tapering inlet chamber of the centrifuge housing protrudes into the central opening.

43. A separator as in claim 42, wherein said core has an upper side comprising an outwardly inclined ring area.

44. A separator as in claim 37, wherein the convex generating line of the side wall of each centrifuge container consists of angularly arranged straight sections, the upper end section extending perpendicularly to the axis of rotation to form a radial upper flange of the side wall, and wherein an annular gap extends between the radial upper flanges of the side wall of the outer centrifuge container and the upper part of the inner centrifuge container, the annular gap forming a passage for separated liquid into an annular channel integrated into the last section of the drain line.

45. A separator as in claim 16 to be inserted into a suction line of a dental system comprising a rinsing basin, wherein a drain line from the rinsing basin enters into the inlet chamber of the centrifuge housing.

46. A separator as in claim 16, further comprising: a liquid collecting container connected to the liquid outlet at the end of the drain line, and a liquid discharge device transferring liquid from the liquid collecting container to the second section of the suction line, that leads to the suction pump with which a separator for liquids and suction air is associated, the liquid discharge device comprising a venturi tube arrangement having a downstream end located in the second section of the suction line.

47. A separator for separating a mixture of solids, liquids and suction air, to be inserted into a suction line of a dental system so that the suction line is divided into two sections, the first section being provided with a suction nozzle discharging the mixture out of a patient, and the second section leading to a suction pump, said separator comprising:
  i) a support having a first line connector to be coupled to the first section of the suction line and a second line connector to be coupled to the second section of the suction line;
  ii) a separator housing detachably arranged on the support and comprising
    an air separating chamber designed as an upper part of the separator housing, the upper part having deflectors, an inlet for the mixture, and an outlet for the separated clean air, said inlet and said outlet tightening to said first and second line connectors, when the separator housing is attached to the support,
    a liquid collecting chamber being arranged beneath the air separating chamber and having a drain opening, and
    a sedimentation chamber for settling the solids up to a predetermined maximum settling level, the sedimentation chamber being provided in a collector bowl detachably mounted on the upper part of the separator housing, the upper edge of the collector bowl being above the drain opening;
  iii) a drain line between the liquid collecting chamber and a liquid outlet at the end of the drain line, said drain line comprising
    several sections, a first section extending upwardly in the liquid collecting chamber, being provided with the drain opening above the predetermined settling level of the solids, and being submersible by accumulated liquid up to a predetermined maximum flood level, and a non-return valve means being arranged in a further section of the drain line and securing against an ingress of unwanted air into the separator housing; and iv) a drain system integrated within the drain line, said system discharging liquid that is accumulated up to the predetermined flood level out of the liquid collecting chamber and transferring said liquid to the liquid outlet.

48. A separator as in claim 47, wherein said support and said upper part of the separator housing, each, comprise horizontally engaging pull out guide means corresponding to each other, the first and second line connectors extending horizontally.

49. A separator as in claim 48, wherein at least one catch means is provided between the upper part of the separator housing and the support.

50. A separator as in claim 47, wherein said upper edge of the detachable collector bowl is provided with a first guide rail, and wherein said upper part of the separator housing is provided with a second guide rail, the first and second guide rail completing to a pull out guide means that engages a corresponding pull out guide means arranged on the support, the pull out guide means of the separator housing and the support, each, as well as the first and second line connectors extending horizontally.

51. A separator as in claim 50, wherein an intermediate section of the drain line is arranged in the support having a third line connector, and wherein the first section of the drain line, which extends upwardly in the liquid collecting chamber, terminates in the upper part of the separator housing and tightens to the third line connector, when the separator housing is attached to the support.

52. A separator as in claim 47, wherein said first and said second line connectors of the support extend perpendicularly to a pull out direction, a region surrounding the inlet for the mixture and surrounding the outlet for the separated clean air, each, of the upper part of the housing as well as a region surrounding the first and the second line connectors, each, being provided with snug fits diverging in pull out direction.

53. A separator as in claim 52, wherein at least one catch means is provided between the upper part of the separator housing and the support.

54. A separator as in claim 47, wherein said drain system discharging liquid out of the liquid collecting chamber comprises an electric pump means inserted into the first section of the drain line, arranged in the upper part of the separator housing, and provided with a power supply means, the power supply means comprising a plug connector arranged between the support and the upper part of the separator housing.

55. A separator as in claim 54, wherein said electric pump is a vane-type impeller pump.

56. A separator as in claim 54, wherein said pump means is actuated by sensors arranged in the liquid collecting chamber and defining a low level corresponding to the position of the drain opening as well as a peak level equal to the predetermined flood level.

57. A separator for separating a mixture of solids, liquids and suction air, to be inserted into a suction line of a dental system so that the suction line is divided into two sections, the first section being provided with a suction nozzle discharging the mixture out of the mouth of a patient, and the second section leading to a suction pump, said separator comprising:

i) a support having a first line connector to be coupled to the first section of the suction line and a second line connector to be coupled to the second section of the suction line;

ii) a separator housing detachably arranged on the support and comprising an air separating chamber designed as an upper part of the separator housing, the upper part having deflectors, an inlet for the mixture, and an outlet for the separated clean air, said inlet and said outlet tightening to said first and second line connectors, when the separator housing is attached to the support, a liquid collecting chamber being arranged beneath the air separating chamber and having a drain opening, and a sedimentation chamber for settling the solids up to a predetermined maximum settling level, the sedimentation chamber being provided in a collector bowl detachably mounted on the upper part of the separator housing the upper edge of the collector bowl being above the drain opening;

iii) a drain line between the liquid collecting chamber and a liquid outlet at the end of the drain line, said drain line comprising several sections, a first section extending upwardly in the liquid collecting chamber, being provided with the drain opening above the predetermined settling level of the solids, and being submersible by accumulated liquid up to a predetermined maximum flood level, a non-return valve means being arranged in a further section of the drain line and securing against an ingress of unwanted air into the separator housing, and a last section terminating at the liquid outlet, a centrifuge housing, that has an inlet chamber and a discharge channel, being detachably inserted into the last section of the drain line and carried by a support plate of the support, the non-return valve means being arranged between the first and the last section of the drain line;

iv) a pump means arranged in the drain line, said pump means discharging liquid that is accumulated up to the predetermined flood level out of the liquid collecting chamber and transferring said liquid to the inlet chamber of the centrifuge housing; and v) a solid bowl centrifuge arranged in the centrifuge housing, said solid bowl centrifuge being provided with a bottom outlet vertically discharging by gravity solids and liquid residues after each working phase of the centrifuge, and with a top liquid outlet passing cleaned liquid into the discharge channel.

58. A separator as in claim 57, wherein an intermediate section of the drain line is arranged in the support having a third line connector, and wherein the first section of the drain line, which extends upwardly in the liquid collecting chamber, terminates in the upper part of the separator housing and tightens to the third line connector, when the separator housing is attached to the support.

59. A separator as in claim 58, wherein an electric pump means discharging liquid out of the liquid collecting chamber is inserted into the first section of the drain line, arranged in the upper part of the separator housing, and is provided with a power supply means, the power supply means comprising a plug connector arranged between the support and the upper part of the separator housing.

60. A separator as in claim 57, wherein at least one intermediate section of the drain line having a fourth line connector is arranged in the support, and wherein an elastic sleeve is removably inserted between the fourth line connector and said inlet chamber to permit detachment of the centrifuge housing.

61. A separator as in claim 57, wherein said liquid outlet is provided at an end piece of the last section of the drain line, said end piece being arranged on the support and having a fifth line connector, and wherein an elastic sleeve is removably inserted between the fifth line connector and said discharge channel to permit detachment of the centrifuge housing.

62. A separator as in claim 61, wherein an intermediate section that is arranged in the support includes a compartment, a sieve intersecting the drain line being arranged removably in the compartment.

63. A separator as in claim 57, wherein said centrifuge housing tapers towards the support plate.

64. A separator as in claim 57, further comprising a feed-back system for cycling liquid residues that are discharging by gravity out of the bottom outlet of the solid bowl centrifuge to the inlet chamber of the centrifuge housing.

65. A separator as in claim 64, wherein said feed-back system comprises a basin for receiving the liquid residues and a connecting line starting from the basin and having an end section terminating at the inlet chamber of the centrifuge housing.

66. A separator as in claim 65, wherein said basin forms a pump housing arranged on the centrifuge housing, the connecting line starting from the pump housing in which a pump means is arranged, the pump housing being removably supported by the support plate of the support.

67. A separator as in claim 66, wherein said pump means comprises an electric vane-type impeller pump.

68. A separator as in claim 66, wherein said connecting line starting from the pump housing comprises a first section leading to a collector bowl that forms a sedimentation chamber and a liquid collecting chamber, and a further suction starting from the liquid collecting chamber, said further section including the end section terminating at the inlet chamber of the centrifuge housing.

69. A separator as in claim 68, wherein said collector bowl is the detachable collector bowl of the separator housing, and wherein said further section of the connecting line is formed by at least one section of the drain line.

70. A separator as in claim 68, wherein a part of the first section of the connecting line is arranged in the support having a sixth and a seventh line connector, the sixth line connector being arranged in the support plate, wherein the pressure side of the pump housing tightens to the sixth line connector, when the centrifuge housing is attached to the support, and wherein an end piece of the first section of the connecting line terminating in the upper part of the separator housing tightens to the seventh line connector, when the upper part of the separator housing is attached to the support.

71. A separator as in claim 57, to be inserted into a suction line of a dental system comprising a rinsing basin, wherein a drain line from the rinsing basin enters into the inlet chamber of the centrifuge housing.

72. A separator as in claim 57, further comprising: a liquid collecting container connected to the liquid outlet at the end of the drain line, and a liquid discharge device transferring liquid from the liquid collecting container to the second section of the suction line that leads to the suction pump with which a separator for liquids and suction air is associated, the liquid discharge device comprising a venturi tube arrangement having a downstream end located in the second section of the suction line.

73. A separator for separating a dental mixture of solids and liquids, which mixture may have been separated from a basic mixture of solids, liquids and suction air being produced in a dental system having a suction pump, a suction line and a suction nozzle discharging said basic mixture out of the mouth of a patient, said separator comprising:
  i) a centrifuge housing having an inlet chamber, a discharge channel, and a basin;
  ii) a solid bowl centrifuge arranged in the centrifuge housing, said solid bowl centrifuge being provided with a bottom outlet vertically discharging by gravity solids and liquid residues into the basin after each working phase of the centrifuge, and with a top liquid outlet passing cleaned liquid into the discharge channel;
  iii) a connecting line having at least a first section and an end section and connecting the bottom outlet of the centrifuge with the inlet chamber of the centrifuge housing, the connecting line being provided with a collector bowl that forms a sedimentation chamber and a liquid residues collecting chamber; and
  iv) a feed back system for cycling liquid residues discharged through the bottom outlet to the inlet chamber of the centrifuge.

74. A separator as in claim 73, wherein said basin is formed by the collector bowl for settling solids, the collector bowl being held detachably at a bottom part of the centrifuge housing.

75. A separator as in claim 73, wherein said feed-back system comprises a pump means that has an intake tube forming the first section of the connecting line and having an intake opening above a predetermined maximum settling level of the collector bowl, the end section, terminating at the inlet chamber of the centrifuge housing, starting from the pressure side of the pump means.

76. A separator as in claim 75, wherein said pump means comprises an electric vane-type impeller pump.

77. A separator as in claim 75, wherein said pump means is actuated by sensors arranged in the liquid collecting chamber and defining a low level corresponding to the position of the intake opening as well as a peak level equal to a predetermined flood level of the intake tube.

78. A separator as in claim 75, wherein said pump means comprises a drive shaft coaxially arranged with the solid bowl centrifuge.

79. A separator as in claim 73, wherein said first section of the connecting line leads to the collecting bowl, and a further section of the connecting line starts from the liquid residues collecting chamber of the collector bowl and includes the end section terminating at the inlet chamber of the centrifuge housing, and wherein said feed-back system comprises a pump means arranged in the basin and transferring the solids and liquid residues into the collector bowl, the first section of the connecting line starting at the pressure side of the pump means.

80. A separator as in claim 79, wherein said pump means comprises an electric vane-type impeller pump.

81. A separator as in claim 79, wherein said collector bowl is an enclosed container being a first part of the further section of the connecting line and having an inlet connected to the first section and an outlet connected to the end section of the connecting line.

82. A separator as in claim 81, wherein said further section of the connecting line comprises a vent tube and a syphon having an intake leg in the liquid residues collecting chamber of the collector bowl.

83. A separator as in claim 79, wherein said feed-back system comprises a second pump means arranged in said further section of the connecting line, said second pump means comprises a self-priming electric pump.

84. A separator as in claim 83, where said second pump means comprises a drive shaft coaxially arranged with the solid bowl centrifuge.

85. A separator as in claim 79, wherein said collector bowl is a detachable top piece of the inlet chamber of the centrifuge housing.

86. A separator as in claim 85, wherein said detachable top piece is an enclosed container having a bottom plate, said enclosed container being a first part of the further section of the connecting line and having an inlet connected to the first section and an outlet connected to the end section of the connecting line.

87. A separator as in claim 86, wherein said end section of the connecting line comprises a tube piece protruding downwardly from the bottom plate, and wherein the inlet chamber of the centrifuge housing comprises a cover plate having an opening, the tube piece projecting through the opening into the inlet chamber of the centrifuge housing.

88. A separator as in claim 87, wherein said tube piece comprises a check valve device opening when the enclosed container is attached on the centrifuge housing and shutting off when the enclosed container is detached.

89. A separator as in claim 87, wherein said enclosed container further comprises a vent tube protruding downwardly from the bottom plate, and wherein the inlet chamber of the centrifuge housing comprises a cover plate having an opening, the vent tube projecting through the opening into the inlet chamber of the centrifuge housing.

90. A separator as in claim 89, wherein said vent tube comprises a check valve device opening when the enclosed container is attached on the centrifuge housing and shutting off when the enclosed container is detached.

91. A separator as in claim 73, wherein said solid bowl centrifuge comprises at least two centrifuge chambers being serially arranged in the drain line and being arranged on a common drive shaft in the centrifuge housing, each centrifuge chamber comprising a solid side wall having a convex line generated by rotation about an axis.

92. A separator as in claim 91, wherein said solid bowl centrifuge comprising two centrifuge chambers formed by single centrifuge containers, said centrifuge containers being arranged in each other.

93. A separator as in claim 92, wherein each centrifuge container comprises a solid side wall held on a core by connecting webs defining gaps, each core being mountable on the drive shaft that is rotatably supported by the centrifuge housing.

94. A separator as in claim 93, wherein the webs of each centrifuge container are arranged between a bottom part of the side wall and the core, and wherein the respective gaps form downwardly directed openings for penetration of liquid and solids.

95. A separator as in claim 93, wherein said core of the outer centrifuge comprises a downwardly protruding sleeve, and wherein the webs of the outer centrifuge container extend upwardly, the respective gaps being formed by slots in the lowest region of the sleeve.

96. A separator as in claim 95, wherein said sleeve has a larger diameter than the core and is connected with the core by a conical part, said conical part comprising an outwardly inclined surface leading liquid and solids into the outer centrifuge container.

97. A separator as in claim 93, wherein the convex generating line of the side wall of each centrifuge container consists of angularly arranged straight sections, the upper end section extending perpendicularly to the axis of rotation to form a radial upper flange of the side wall, and wherein an annular gap extends between the radial upper flanges of the side wall of the outer centrifuge container and the upper part of the inner centrifuge container, the annular gap forming a passage for separated liquid into an annular channel being part of the top liquid outlet.

98. A separator as in claim 93, wherein the side wall of said inner centrifuge container upwardly protrudes the core and defines a central opening, and wherein the annular sleeve of the downwardly tapering inlet chamber of the centrifuge housing protrudes into the central opening.

99. A separator as in claim 73, to be used with a dental system comprising a rinsing basin, wherein a drain line from the rinsing basin enters into the inlet chamber of the centrifuge housing.

100. A separator as in claim 73, when said mixture having been separated from said basic mixture further comprising: a liquid collecting container connected to the liquid outlet at the end of the drain line, and a liquid discharge device transferring liquid from the liquid collecting container to said second section of the suction line, that leads to the suction pump with which a separator for liquids and suction aid is associated, the liquid discharge device comprising a venturi tube arrangement having a downstream end located in the second section of the suction line.

101. A separator for separating a mixture of solids, liquids and suction air, to be inserted into a suction line of a dental system so that the suction line is divided into two sections, the first section being provided with a suction nozzle discharging the mixture out of the mouth of a patient, and the second section leading to a suction pump with which a separator for liquids and suction air is associated, separated clean liquid being feedable into the second section of the suction line, said separator comprising
   i) a separator housing comprising
      an air separating chamber designed as an upper part of the separator housing, the upper part having deflectors, an inlet for the mixture to be connected to the first section of the suction line, and an outlet for the separated clean air to be connected to the second section of the suction line, a liquid collecting chamber arranged beneath the air separating chamber and having a drain opening, and a sedimentation chamber for settling the solids up to a predetermined maximum settling level, the sedimentation chamber being provided in a collector bowl detachably mounted on the upper part of the separator housing, the upper edge of the collector bowl being above the drain opening;

ii) a drain line comprising a first section extending upwardly in the separator housing and provided with the drain opening above the predetermined settling level of the solids, and a liquid outlet being associated with the second section of the suction line; and iii) a discharge device arranged in the drain line and transferring separated liquid from the liquid collecting chamber to the second section of the suction line that leads to the suction pump.

102. A separator as in claim 101, wherein said deflectors are formed by at least one cross-bar arranged in the upper part of the separator housing.

103. A separator as in claim 104, wherein said inlet for the mixture comprising an upstream end and a downstream end has a cross-section diverging towards the downstream end adjacent the air separating chamber.

104. A separator as in claim 101, wherein said discharge device transferring separated liquid to the second section of the suction line comprises a venturi tube arrangement forming the upwardly extending section of the drain line and having the liquid outlet located in the outlet for the separated clean air to be connected to the second section of the suction line.

105. A separator as in claim 101, wherein said separator housing further comprises a secondary tank forming an intermediate section of the drain line, said secondary tank being associated with the liquid collecting chamber and being open into the air separating chamber, the discharge device comprising a liquid transfer system between the liquid collecting chamber and the secondary tank.

106. A separator as in claim 105, wherein said discharge device transferring separated liquid to the second section of the suction line comprises a venturi tube arrangement forming an upwardly extending section of the drain line arranged in the secondary tank and having the liquid outlet in the outlet for the separated clean air to be connected to the second section of the suction line.

107. A separator as in claim 105, wherein said separator housing further comprises a housing cover and a partition that ends at a distance from the housing cover and separates the secondary tank from the liquid collecting chamber, the liquid transfer system being arranged in the partition.

108. A separator as in claim 107, wherein said liquid transfer system comprises a syphon having an intake leg and an overflow level, said first section forming the intake leg of the syphon, and wherein the syphon is inserted into the partition, the overflow level of the syphon lying beneath the upper edge of the partition.

109. A separator as in claim 101, wherein said air separating chamber having deflectors, a cyclone arrangement that has a helical path being formed in the air separating chamber, the outlet for separated clean air which includes a suction trunk being centrally arranged within the helical path and being closeable by an axially guided sealing member.

110. A separator as in claim 109, wherein said axially guided sealing member is held in sealing position by the force of a spring and is held in open position by a vacuum created by the suction pump, a control system releasing the vacuum when accumulated liquid exceeds a predetermined maximum level in the liquid collecting chamber of the separator housing.

111. A separator as in claim 101, wherein said collector bowl having a side wall and a bottom wall comprises at least one wall region that is displaceable between an inwardly and an outwardly projecting position thereby altering the volume of the collector bowl.

112. A separator as in claim 111, wherein each displaceable region is provided with a handle.

113. A separator as in claim 112, wherein said handle is arranged inside the superficial area of the collector bowl when the wall region is displaced inwardly.

114. A separator as in claim 113, wherein said collector bowl comprises two displaceable regions at opposite sides of the side wall.

115. A method for separating a dental mixture of a solid and a liquid component by means of a separator, said mixture being transported by suction air produced in a dental system having a suction pump, said solid component being collected and said liquid component being passed through in a defined flow direction and discharged to waste, said method comprising:

i) separating the suction air from the mixture, passing the mixture into a sedimentation chamber and settling at least most of the solid component, ii) removing the liquid component accumulated above a predetermined settling level of the solid component; and iii) separating residues of the solid component from said liquid component removed in step ii) and being passed at least in step ii) and iii) without reverse of said flow direction.

116. The method as set forth in claim 115, wherein step iii) comprises passing the liquid component and the residues of the solid component into a second sedimentation chamber, settling the residues of the solid component, and removing against the reduced pressure of the suction pump the liquid component accumulated above a predetermined settling level.

117. The method as set forth in claim 115, wherein step iii) comprises passing against the reduced pressure of the suction pump the liquid component and the residues of the solid component into a centrifuge, centrifugating in centrifugal phases the liquid component under air pressure, and discharging by gravity after each centrifuged phase the residues of the solid component and residues of the liquid component.

118. The method as set forth in claim 117 further comprising the step of:

iv) separating said residues of the liquid and solid components separated in step iii).

119. The method as set forth in claim 115, wherein step iii) further comprises cycling said residues of the liquid and the solid components.

120. The method as set forth in claim 119, wherein the suction air is used to cycle said residues to step i).

121. A method for separating a dental mixture of a solid and a liquid component by means of a separator, said solid component being collected and said liquid component being passed through in a defined flow direction and discharged to waste, said method comprising:
i) centrifugating the mixture in centrifugal phases, discharging the solid component by gravity after each centrifugal phase into a collector bowl; and
ii) separating from the solid component residues of the liquid component being passed through the separator without reverse of said defined flow direction.

122. The method as set forth in claim 121, wherein step ii) comprises passing the discharged solid component and residues of the liquid component into a sedimentation chamber, and settling at least most of the solid component.

123. The method as set forth in claim 122 further comprising the step of:
iii) separating residues of the solid component from said residues of the liquid component separated in step ii).

124. The method as set forth in claim 123, wherein step iii) further comprises cycling residues of the liquid component accumulated above a predetermined settling level and of the solid component to step i).

* * * * *